US010450369B2

(12) United States Patent
Saldanha et al.

(10) Patent No.: US 10,450,369 B2
(45) Date of Patent: *Oct. 22, 2019

(54) HUMANIZED ANTIBODIES THAT RECOGNIZE ALPHA-SYNUCLEIN

(71) Applicant: PROTHENA BIOSCIENCES LIMITED, Dublin (IE)

(72) Inventors: Jose William Saldanha, Enfield (GB); Tarlochan S. Nijjar, Orinda, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/857,104

(22) Filed: Dec. 28, 2017

(65) Prior Publication Data
US 2018/0201669 A1 Jul. 19, 2018

Related U.S. Application Data

(60) Division of application No. 15/387,580, filed on Dec. 21, 2016, now Pat. No. 9,884,906, which is a division of application No. 14/156,441, filed on Jan. 15, 2014, now Pat. No. 9,556,259, which is a division of application No. 13/662,261, filed on Oct. 26, 2012, now Pat. No. 8,609,820, which is a continuation of application No. PCT/US2012/062290, filed on Oct. 26, 2012.

(60) Provisional application No. 61/711,208, filed on Oct. 8, 2012, provisional application No. 61/553,131, filed on Oct. 28, 2011.

(51) Int. Cl.
A61K 39/00 (2006.01)
A61P 25/16 (2006.01)
C07K 16/18 (2006.01)
G01N 33/68 (2006.01)

(52) U.S. Cl.
CPC .............. C07K 16/18 (2013.01); A61P 25/16 (2018.01); G01N 33/6854 (2013.01); G01N 33/6896 (2013.01); A61K 2039/505 (2013.01); C07K 2317/24 (2013.01); C07K 2317/34 (2013.01); C07K 2317/565 (2013.01); C07K 2317/567 (2013.01); C07K 2317/76 (2013.01); G01N 2800/2835 (2013.01)

(58) Field of Classification Search
None
See application file for complete search history.

(56) References Cited

U.S. PATENT DOCUMENTS

| 6,719,971 | B1 | 4/2004 | Carter et al. |
|---|---|---|---|
| 6,881,557 | B2 | 4/2005 | Foote et al. |
| 7,022,500 | B1 | 4/2006 | Queen et al. |
| 7,358,331 | B2 | 4/2008 | Chilcote et al. |
| 7,566,771 | B1 | 7/2009 | Adair et al. |
| 7,657,380 | B2 | 2/2010 | Lazar et al. |
| 7,674,599 | B2 | 3/2010 | Chilcote et al. |
| 7,910,333 | B2 | 3/2011 | Chilcote et al. |
| 7,919,088 | B2 | 4/2011 | Schenk et al. |
| 8,092,801 | B2 | 1/2012 | Schenk et al. |
| 8,609,820 | B2 | 12/2013 | Saldanha et al. |
| 8,790,644 | B2 | 7/2014 | Saldanha et al. |
| 9,217,030 | B2 | 12/2015 | Saldanha et al. |
| 9,234,031 | B2 | 1/2016 | Saldanha et al. |
| 9,556,259 | B2 | 1/2017 | Saldanha et al. |
| 9,605,056 | B2 | 3/2017 | Barbour et al. |
| 9,670,273 | B2 | 6/2017 | Saldanha et al. |
| 9,884,906 | B2 | 2/2018 | Saldanha et al. |
| 10,081,674 | B2 | 9/2018 | Barbour et al. |
| 10,084,674 | B2 | 9/2018 | Barbour et al. |
| 10,118,960 | B2 | 11/2018 | Saldanha et al. |
| 2006/0008883 | A1 | 1/2006 | Lazar et al. |
| 2008/0014194 | A1 | 1/2008 | Schenk et al. |
| 2009/0010924 | A1 | 1/2009 | Wu et al. |
| 2009/0202432 | A1 | 8/2009 | Schenk et al. |
| 2009/0208487 | A1 | 8/2009 | Schenk et al. |
| 2010/0031377 | A1 | 2/2010 | Schenk et al. |
| 2010/0086545 | A1 | 4/2010 | Schenk et al. |
| 2010/0098712 | A1 | 4/2010 | Adler et al. |
| 2010/0203631 | A1 | 8/2010 | Chilcote et al. |
| 2011/0052498 | A1 | 3/2011 | Lannfelt et al. |
| 2012/0204275 | A1 | 8/2012 | Schenk |
| 2012/0276019 | A1 | 11/2012 | Charles et al. |
| 2014/0127131 | A1 | 5/2014 | Barbour et al. |
| 2014/0275495 | A1 | 9/2014 | Saldanha et al. |
| 2015/0024433 | A1 | 1/2015 | Saldanha et al. |
| 2015/0056187 | A1 | 2/2015 | Saldanha et al. |
| 2015/0079074 | A1 | 3/2015 | Garidel et al. |
| 2015/0259404 | A1 | 9/2015 | Barbour et al. |
| 2016/0251416 | A1 | 9/2016 | Saldanha et al. |
| 2018/0016329 | A1 | 1/2018 | Saldanha et al. |
| 2018/0201669 | A1 | 7/2018 | Saldanha et al. |

FOREIGN PATENT DOCUMENTS

| EP | 2234600 B1 | 8/2014 |
|---|---|---|
| JP | H4-217630 | 8/1992 |
| JP | 2000-510813 | 8/2000 |
| JP | 2008-520551 | 6/2008 |
| JP | 2013-5000976 | 1/2013 |
| JP | 2013-504540 | 2/2013 |
| JP | 2013-521769 | 6/2013 |
| JP | 2014-522843 | 9/2014 |
| JP | 2011-246484 | 12/2014 |
| WO | WO 2004/039234 A2 | 5/2004 |
| WO | WO 2004/041067 | 5/2004 |
| WO | WO 2005/047860 A2 | 5/2005 |
| WO | WO 2007/011907 A2 | 1/2007 |
| WO | WO 2008/011348 A2 | 1/2008 |
| WO | WO 2008/103472 A2 | 8/2008 |

(Continued)

OTHER PUBLICATIONS

Masliah et al., "Effects of α-Synuclein Immunization in a Mouse Model of Parkinson's Disease", Neuron, 46:857-866, (2005).

(Continued)

Primary Examiner — Adam Weidner
(74) Attorney, Agent, or Firm — Alston & Bird LLP

(57) ABSTRACT

The present application discloses humanized 9E4 antibodies. The antibodies bind to human alpha synuclein and can be used for immunotherapy of Lewy body disease.

43 Claims, 8 Drawing Sheets

Specification includes a Sequence Listing.

(56) References Cited

FOREIGN PATENT DOCUMENTS

| | | |
|---|---|---|
| WO | WO 2008/116103 A2 | 9/2008 |
| WO | WO 2010/069603 A1 | 6/2010 |
| WO | WO 2011/090720 A2 | 7/2011 |
| WO | WO 2011/107544 A1 | 9/2011 |
| WO | WO 2011/127324 A2 | 10/2011 |
| WO | WO 2011/155607 A1 | 12/2011 |
| WO | WO 2011/156328 A1 | 12/2011 |
| WO | WO 2012/009631 A1 | 1/2012 |
| WO | WO 2012/160536 A1 | 11/2012 |
| WO | WO 2012/177997 A1 | 12/2012 |
| WO | WO 2013/063516 A1 | 5/2013 |
| WO | WO 2013/066866 A1 | 5/2013 |
| WO | WO 2013/112945 A1 | 8/2013 |
| WO | WO 2014/033074 A1 | 3/2014 |
| WO | WO 2014/058924 A2 | 4/2014 |
| WO | WO 2015/001504 A2 | 1/2015 |
| WO | WO 2015/155694 A1 | 10/2015 |

OTHER PUBLICATIONS

Masliah et al., "Passive Immunization Reduces Behavioral and Neuropathological Deficits in an Alpha-Synuclein Transgenic Model of Lewy Body Disease", *PLoS ONE*, 6(4):e19338, pp. 1-17, (Apr. 2011).
PCT/US2002/062290 Written Opinion and Search Report dated Jan. 28, 2013.
PCT/US2013/023307 Written Opinion and Search Report dated May 13, 2013.
Finlay et al., "Affinity Maturation of a Humanized Rat Antibody for Anti-RAGE Therapy: Comprehensive Mutagenesis Reveals a Hight Level of Mutational Plasticity Both Inside and Outside the Complementarity-Determining Regions", *J.Mol. Biol.*, 388, pp. 541-558, (2009).
PCT/US2013/063945 Written Opinion and Search Report dated Apr. 22, 2014.
PCT/US2013/063945 Invitation to Pay Additional Fees dated Feb. 6, 2014.
Mihara, et al., "CTLA4Ig inhibits T cell-dependent B-cell maturation in murine systemic lupus erythematosus," J. Clin. Invest., vol. 106, No. 1, pp. 91-101 (2000).
Hackett, et al., "Recombinant Mouse-Human Chimeric Antibodies as Calibrators in Immunoassays That Measure Antibodies to *Toxoplasma gondii*," *J. Clin. Microbiol.*, vol. 36, No. 5, pp. 1277-1284 (1998).
Yang, et al., "Structural basis of immunosuppression by the therapeutic antibody daclizumab," *Cell Research*, 20:1361-1371 (2010).
Genbank Accession No. AAC28255.1, "Immunoglobulin kappa light chain [Mus musculus]," Dec. 15, 1999.
Genbank Accession No. 3NFP A, "Chain A, Crystal Structure of the Fab Fragment of Therapeutic Antibody Daclizumab in Complex With Il-2ra (cd25) Ectodomain," Oct. 19, 2013.
Genbank Accession No. AAF88044.1, "Immunoglobulin heavy chain variable regions [Mus musculus]," Jul. 27, 2000.
Choi, et al., "Fine epitope mapping of monoclonal antibodies specific to human alpha-synuclein," Neurosci Lett., 17;397(1-2):53-58 (2006) Abstract only.
Gonzalas, et al., "SDR grafting of a murine antibody using multiple human germine templates to minimize its immunogenicity," Molecular Immunology, 41:863-872 (2004).
PCT/US2013/023307 International Preliminary Report on Patentability and Written Opinion dated Jul. 29, 2014.
U.S. Appl. No. 12/156,441 Non-Final Office Action dated Nov. 10, 2014.
U.S. Appl. No. 14/049,169 Restriction Requirement dated Jul. 16, 2014.
PCT/IB2014/062806 Invitation to Pay Additional Fees and Where Applicable Protest Fee dated Oct. 29, 2014.
Wang, W., "Instability, stabilization, and formulation of liquid protein pharmaceuticals," Int. J. Pharmaceutics, 185(2):129-188 (1999).
Wang, et at., "Antibody Structure, Instability, and Formulation", Journal of Pharmaceutical Sciences, vol. 96:1 pp. 1-26 (Jan. 2007).
Warne, et al., "Development of high concentration protein biopharmaceuticals: The use of platform approaches in formulation development," *European Journal of Pharmaceutics and Biopharmaceutics*, 78:202-212 (2011).
Daugherty, et al., "Formulation and Delivery Issues for Monoclonal Antibody Therapeutics," *Advanced Drug Delivery Reviews*, 58(5-6):686-42 (2006) with permission Elsevier.
LBD Association, Inc. 2013, "Incidence of lewy body dementias in a general population", http://222.lbda.org.
PCT/IB2014/062806 International Search Report and Written Opinion of the International Searching Authority dated Apr. 24, 2015.
EP 12844433.8 European Search Report dated Feb. 17, 2015.
U.S. Appl. No. 14/340,342 Non-Final Office Action dated Mar. 3, 2015.
U.S. Appl. No. 14/049,169 Non-Final Office Action dated Feb. 10, 2015.
Wang, "Advances in the production of human monoclonal antibodies," Antibody Technology Journal, 1: 1-4 (2011).
EP 13740871.2 European Search Report dated Jun. 3, 2015.
Nasstrom, et al., "Antibodies against Alpha-synuclein Reduce Oligomerization in Living Cells," *PloS ONE*, vol. 6, Issue 10, e27230 (Oct. 2011).
U.S. Appl. No. 14/340,555 Non-Final Office Action dated Apr. 8, 2015.
U.S. Appl. No. 14/049,169 Final Office Action and Telephone Interview dated Oct. 2, 2015.
PCT/IB2015/052524 Search Report and Written Opinion dated Jul. 3, 2015.
U.S. Appl. No. 14/156,441 Final Office Action dated Jun. 8, 2016.
U.S. Appl. No. 14/049,169 Non-Final Office Action dated Mar. 30, 2016.
U.S. Appl. No. 14/322,797 Restriction Requirement dated Aug. 29, 2016.
EP13845625 European Extended Search Report dated Jul. 18, 2016.
U.S. Appl. No. 14/156,441 Notice of Allowance dated Sep. 20, 2016.
U.S. Appl. No. 14/937,792 Non-Final Office Action dated Aug. 30, 2016.
U.S. Appl. No. 14/937,792 Examiner Initiated Interview Summary dated Aug. 30, 2016.
U.S. Appl. No. 14/937,792 Examiner Initiated Interview Summary dated Feb. 2, 2017.
U.S. Appl. No. 14/937,792 Notice of Allowance dated Feb. 2, 2017.
U.S. Appl. No. 14/156,441 Examiner Initiated Interview Summary dated Nov. 10, 2014.
U.S. Appl. No. 14/049,169 Examiner Initiated Interview Summary dated Feb. 10, 2015.
U.S. Appl. No. 14/049,169 Examiner Initiated Interview Summary dated Oct. 2, 2015.
U.S. Appl. No. 14/049,169 Examiner Initiated Interview Summary dated Nov. 1, 2016.
U.S. Appl. No. 14/049,169 Notice of Allowance dated Nov. 1, 2016.
U.S. Appl. No. 14/322,797 Non-Final Office Action dated Jan. 3, 2017.
PCT/US2013/063945 International Preliminary Report on Patentability dated Apr. 8, 2015.
PCT/US2012/062290 International Preliminary Report on Patentability dated Apr. 29, 2014.
PCT/IB2014/062806 International Preliminary Report on Patentability dated Jan. 5, 2016.
PCT/IB2015/052524 International Preliminary Report on Patentability dated Oct. 12, 2016.
Zhang et al., "Conformation-dependent scFv antibodies specifically recognize the oligomers assembled from various amyloids and show colocalization of amyloid fibrils with oligomers in patients with amyloidoses," Biochimica et Biophysica Acta (BBA)—Protein & Proteomics, 1814(2):1703-1712, (2011).
Jones et al., "Deimmunization of Monoclonal Antibodies," *Therapeutic Antibodies: Methods and Protocols*, 525:405-423, (2009).
EP 13845625.6 Supplementary European Search Report completed Jul. 7, 2016.

(56) References Cited

OTHER PUBLICATIONS

Roche Data Sheet, "Herceptin 140625" Prepared Jun. 25, 2014.
Xolair, "Highlights of Prescribing Information", Genentech, Inc. (2003).
U.S. Appl. No. 15/387,580 Notice of Allowance dated Sep. 28, 2017.
U.S. Appl. No. 15/429,962 Non-Final Office Action dated Sep. 22, 2017.
U.S. Appl. No. 14/322,797 Final Office Action dated Jul. 19, 2017.
Mahler, et al., "Trends n Formulation and Drug Delivery for Antibodies", Process Scale Purification of Antibodies, Second Edition, Edited by Uwe Gottschalk, 2017 John Wiley & Sons, Inc. Published 2017 by John Wiley & Sons, Inc.
U.S. Appl. No. 14/322,797 Non-Final Office Action dated Mar. 2, 2018.
U.S. Appl. No. 15/429,962 Notice of Allowance and Interview Summary dated May 21, 2018.
Amgen, Inc., Blincyto® (blinatumomab) Highlights of Prescribing Information and Full Prescribing Information revised May 2018.
U.S. Appl. No. 15/587,255 Notice of Allowance and Examiner Initiated Interview Summary dated Jun. 27, 2018.
U.S. Appl. No. 14/322,797 Final Office Action dated Aug. 7, 2018.

Fig. 1

9E4 VH alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m9E4VH | E | V | K | L | V | E | S | G | G | G | L | V | K | P | G | A | S | L | K | L |
| 1791009 | E | V | Q | L | V | E | S | G | G | G | L | V | Q | P | G | G | S | L | R | L |
| Hu9E4VHv1 | E | V | Q | L | V | E | S | G | G | G | L | V | Q | P | G | G | S | L | R | L |
| Hu9E4VHv2 | E | V | Q | L | V | E | S | G | G | G | L | V | Q | P | G | G | S | L | R | L |
| Hu9E4VHv3 | E | V | Q | L | V | E | S | G | G | G | L | V | Q | P | G | G | S | L | R | L |
| Hu9E4VHv4 | E | V | Q | L | V | E | S | G | G | G | L | V | Q | P | G | G | S | L | R | L |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m9E4VH | S | C | A | A | S | G | F | T | F | S | *N* | *Y* | *G* | *M* | *S* | W | V | R | Q | T |
| 1791009 | S | C | A | A | S | G | F | T | F | S | *S* | *Y* | *W* | *M* | *S* | W | V | R | Q | A |
| Hu9E4VHv1 | S | C | A | A | S | G | F | T | F | S | *N* | *Y* | *G* | *M* | *S* | W | V | R | Q | A |
| Hu9E4VHv2 | S | C | A | A | S | G | F | T | F | S | *N* | *Y* | *G* | *M* | *S* | W | V | R | Q | A |
| Hu9E4VHv3 | S | C | A | A | S | G | F | T | F | S | *N* | *Y* | *G* | *M* | *S* | W | V | R | Q | A |
| Hu9E4VHv4 | S | C | A | A | S | G | F | T | F | S | *N* | *Y* | *G* | *M* | *S* | W | V | R | Q | A |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m9E4VH | S | D | K | R | L | E | W | V | A | *S* | *I* | *S* | *Q* | *S* | *G* | *S* | *S* | *T* | *Y* | *Y* |
| 1791009 | P | G | K | G | L | E | W | V | A | *N* | *I* | *K* | *Q* | *D* | *G* | *S* | *E* | *K* | *Y* | *Y* |
| Hu9E4VHv1 | P | G | K | G | L | E | W | V | A | *S* | *I* | *S* | *Q* | *G* | *G* | *S* | *S* | *T* | *Y* | *Y* |
| Hu9E4VHv2 | P | G | K | G | L | E | W | V | A | *S* | *I* | *S* | *Q* | *G* | *G* | *S* | *S* | *T* | *Y* | *Y* |
| Hu9E4VHv3 | P | G | K | G | L | E | W | V | A | *S* | *I* | *S* | *Q* | *G* | *G* | *S* | *S* | *T* | *Y* | *Y* |
| Hu9E4VHv4 | P | G | K | G | L | E | W | V | A | *S* | *I* | *S* | *Q* | *G* | *G* | *S* | *S* | *T* | *Y* | *Y* |

Fig. 1 (cont.)

9E4 VH alignment

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m9E4VH    | P | D | N | V | K | G | R | F | T | I | S | R | E | D | A | K | N | T | L | Y |
| 1791009   | V | D | S | V | K | G | R | F | T | I | S | R | D | N | A | K | N | S | L | Y |
| Hu9E4VHv1 | P | D | N | V | K | G | R | F | T | I | S | R | D | D | A | K | N | S | L | Y |
| Hu9E4VHv2 | P | D | N | V | K | G | R | F | T | I | S | R | D | N | A | K | N | S | L | Y |
| Hu9E4VHv3 | P | D | N | V | K | G | R | F | T | I | S | R | D | D | A | K | N | S | L | Y |
| Hu9E4VHv4 | P | D | N | V | K | G | R | F | T | I | S | R | D | N | A | K | N | S | L | Y |

| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m1H7VH    | L | Q | M | S | S | L | R | S | E | D | T | A | L | Y | Y | C | S | R | G | G |
| 1791009   | L | Q | M | N | S | L | R | A | E | D | T | A | V | Y | Y | C | C | R | G | S |
| Hu9E4VHv1 | L | Q | M | N | S | L | R | A | E | D | T | A | V | Y | Y | C | S | R | G | G |
| Hu9E4VHv2 | L | Q | M | N | S | L | R | A | E | D | T | A | V | Y | Y | C | S | R | G | G |
| Hu9E4VHv3 | L | Q | M | N | S | L | R | A | E | D | T | A | V | Y | Y | C | A | R | G | G |
| Hu9E4VHv4 | L | Q | M | N | S | L | R | A | E | D | T | A | V | Y | Y | C | A | R | G | G |

| Kabat Numbering | 97 | 98 | 99 | 100 | 101 | 102 | 103 | 104 | 105 | 106 | 107 | 108 | 109 | 110 | 111 | 112 | 113 | 114 |
|---|---|---|---|---|---|---|---|---|---|---|---|---|---|---|---|---|---|---|
| m9E4VH    | A | G | I | - | D | Y | W | G | Q | G | T | T | L | T | V | S | S | - |
| 1791009   | S | D | M | - | D | Y | W | G | Q | G | T | L | V | T | V | S | S | - |
| Hu9E4VHv1 | A | G | I | - | D | Y | W | G | Q | G | T | L | V | T | V | S | S | - |
| Hu9E4VHv2 | A | G | I | - | D | Y | W | G | Q | G | T | L | V | T | V | S | S | - |
| Hu9E4VHv3 | A | G | I | - | D | Y | W | G | Q | G | T | L | V | T | V | S | S | - |
| Hu9E4VHv4 | A | G | I | - | D | Y | W | G | Q | G | T | L | V | T | V | S | S | - |

Fig. 2

9E4 VL alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m9E4VL | D | S | V | M | S | Q | S | P | S | S | L | A | V | S | V | G | E | K | V | T |
| 63102889 | D | H | Q | M | T | Q | S | P | S | S | L | S | A | S | V | G | D | R | V | T |
| Hu9E4VLv1 | D | H | Q | M | T | Q | S | P | S | S | L | S | A | S | V | G | D | R | V | T |
| Hu9E4VLv2 | D | H | Q | M | T | Q | S | P | S | S | L | S | A | S | V | G | D | R | V | T |
| Hu9E4VLv3 | D | H | Q | M | T | Q | S | P | S | S | L | S | A | S | V | G | D | R | V | T |

| Kabat Numbering | 21 | 22 | 23 | 24 | 25 | 26 | 27 | 27A | 27B | 27C | 27D | 27E | 27F | 28 | 29 | 30 | 31 | 32 | 33 | 34 |
|---|---|---|---|---|---|---|---|---|---|---|---|---|---|---|---|---|---|---|---|---|
| m9E4VL | M | S | C | *K* | *S* | *H* | *Q* | *T* | *L* | *L* | *Y* | *S* | *S* | *N* | *Q* | *K* | *S* | *Y* | *L* | *A* |
| 63102889 | I | T | C | *R* | *A* | *S* | *Q* | – | – | – | – | – | – | *S* | *I* | *S* | *N* | *Y* | *L* | *N* |
| Hu9E4VLv1 | I | T | C | *K* | *S* | *I* | *Q* | *T* | *L* | *L* | *Y* | *S* | *S* | *N* | *Q* | *K* | *N* | *Y* | *L* | *A* |
| Hu9E4VLv2 | I | T | C | *K* | *S* | *I* | *Q* | *T* | *L* | *L* | *Y* | *S* | *S* | *N* | *Q* | *K* | *N* | *Y* | *L* | *A* |
| Hu9E4VLv3 | I | T | C | *K* | *S* | *I* | *Q* | *T* | *L* | *L* | *Y* | *S* | *S* | *N* | *Q* | *K* | *N* | *Y* | *L* | *A* |

| Kabat Numbering | 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|---|
| m9E4VL | W | F | Q | Q | K | P | G | Q | S | P | K | L | L | H | Y | *W* | *A* | *S* | *I* | *R* |
| 63102889 | W | Y | Q | Q | K | P | G | K | A | P | K | L | L | H | Y | *A* | *A* | *S* | *S* | *L* |
| Hu9E4VLv1 | W | F | Q | Q | K | P | G | K | A | P | K | L | L | H | Y | *W* | *A* | *S* | *I* | *R* |
| Hu9E4VLv2 | W | Y | Q | Q | K | P | G | K | A | P | K | L | L | H | Y | *W* | *A* | *S* | *I* | *R* |
| Hu9E4VLv3 | W | F | Q | Q | K | P | G | K | A | P | K | L | L | H | Y | *W* | *A* | *S* | *I* | *R* |

Fig. 2 (cont.)

9E4 VL alignment

| Kabat Numbering | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|
| m9E4VL | K | S | G | V | P | D | R | F | T | G | S | G | S | G | T | D | F | T | L | T |
| 63102889 | Q | S | G | V | P | S | R | F | S | G | S | G | S | G | T | D | F | T | L | T |
| Hu9E4VLv1 | K | S | G | V | P | S | R | F | S | G | S | G | S | G | T | D | F | T | L | T |
| Hu9E4VLv2 | K | S | G | V | P | S | R | F | S | G | S | G | S | G | T | D | F | T | L | T |
| Hu9E4VLv3 | K | S | G | V | P | S | R | F | S | G | S | G | S | G | T | D | F | T | L | T |

| Kabat Numbering | 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|
| m9E4VL | I | S | S | V | K | A | E | D | L | A | V | Y | Y | C | Q | Q | Y | Y | S | Y |
| 63102889 | I | S | S | L | Q | P | E | D | F | A | T | Y | Y | C | Q | Q | S | Y | S | T |
| Hu9E4VLv1 | I | S | S | L | Q | P | E | D | F | A | T | Y | Y | C | Q | Q | Y | Y | S | Y |
| Hu9E4VLv2 | I | S | S | L | Q | P | E | D | F | A | T | Y | Y | C | Q | Q | Y | Y | S | Y |
| Hu9E4VLv3 | I | S | S | L | Q | P | E | D | L | A | T | Y | Y | C | Q | Q | Y | Y | S | Y |

| Kabat Numbering | 95 | 96 | 97 | 98 | 99 | 100 | 101 | 102 | 103 | 104 | 105 | 106 | 107 |
|---|---|---|---|---|---|---|---|---|---|---|---|---|---|
| m9E4VL | P | L | T | F | G | A | G | T | K | L | E | L | K |
| 63102889 | P | L | T | F | G | G | G | T | K | L | E | H | K |
| Hu9E4VLv1 | P | L | T | F | G | G | G | T | K | L | E | H | K |
| Hu9E4VLv2 | P | L | T | F | G | G | G | T | K | L | E | H | K |
| Hu9E4VLv3 | P | L | T | F | G | G | G | T | K | L | E | H | K |

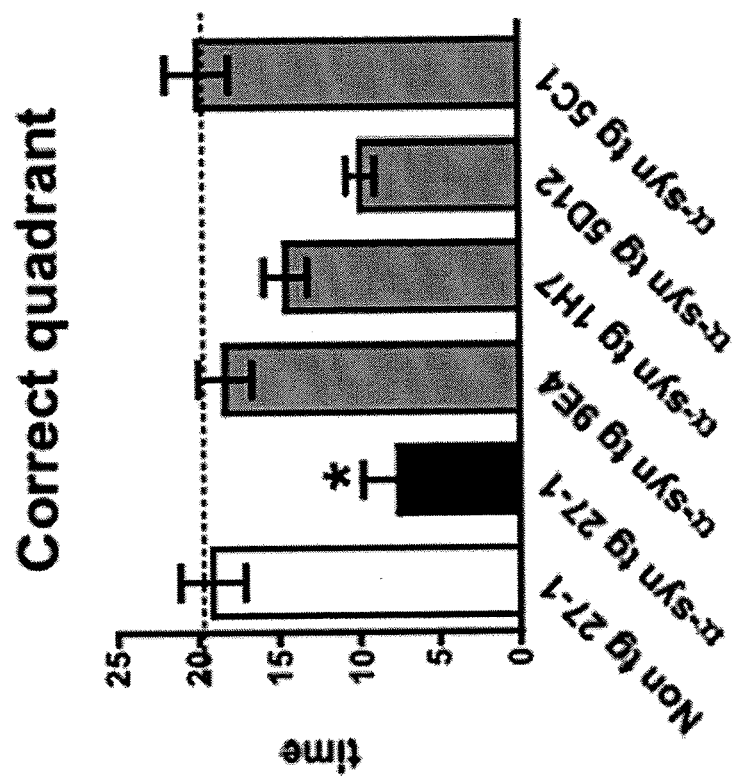
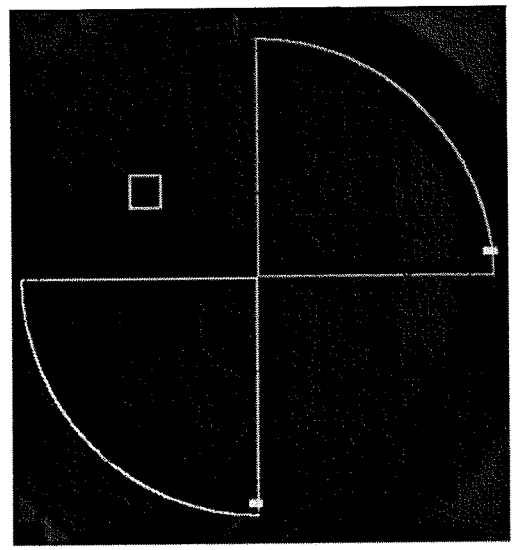
Fig. 3

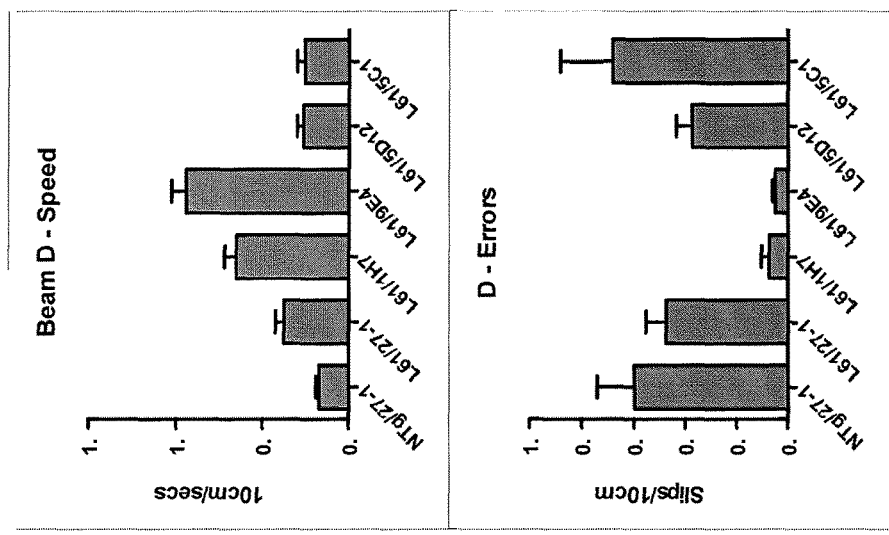
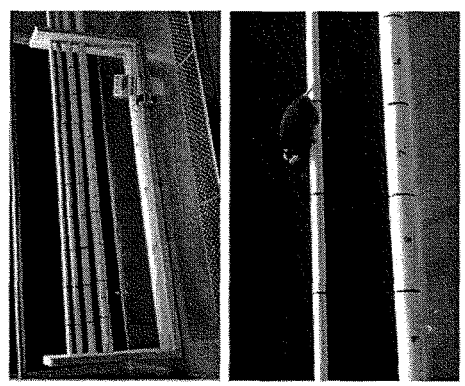
Fig. 4

HUMANIZED ANTIBODIES THAT RECOGNIZE ALPHA-SYNUCLEIN

CROSS-REFERENCE TO RELATED APPLICATION

This application is a divisional of U.S. Ser. No. 15/387,580 filed Dec. 21, 2016, which is a divisional of U.S. Ser. No. 14/156,441 filed Jan. 15, 2014, which is a divisional of U.S. Ser. No. 13/662,261, which claims priority to U.S. 61/553,131 filed Oct. 28, 2011, and U.S. 61/711,208, filed Oct. 8, 2012, each of which is incorporated by reference in the entirety for all purposes. U.S. Ser. No. 14/156,441 is also a continuation of PCT/US12/62290, filed Oct. 26, 2012, which claims priority to U.S. Ser. No. 61/553,131 filed Oct. 28, 2011, and U.S. Ser. No. 61/711,208, filed Oct. 8, 2012.

REFERENCE TO A SEQUENCE LISTING

The Sequence Listing written in file 507250_SEQLIST-.txt is 35,297 bytes and was created on Dec. 27, 2017. The information contained in this file is hereby incorporated by reference.

BACKGROUND

Synucleinopathies also known as Lewy body diseases (LBDs), are characterized by degeneration of the dopaminergic system, motor alterations, cognitive impairment, and formation of Lewy bodies (LBs) and/or Lewy neurites. (McKeith et al., Neurology (1996) 47:1113-24). Synucleinopathies include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease, pure autonomic failure and multiple system atrophy (MSA; e.g., Olivopontocerebellar Atrophy, Striatonigral Degeneration and Shy-Drager Syndrome). Several nonmotor signs and symptoms are thought to be harbingers for synucleinopathies in the prodromal phase of the diseases (i.e, the presymptomatic, subclinical, preclinical, or premotor period). Such early signs include, for example, REM sleep behavior disorder (RBD), loss of smell and constipation (Mahowald et al., Neurology (2010) 75:488-489). Lewy body diseases continue to be a common cause for movement disorders and cognitive deterioration in the aging population (Galasko et al., Arch. Neurol. (1994) 51:888-95).

Alpha-synuclein is part of a large family of proteins including beta- and gamma-synuclein and synoretin. Alpha-synuclein is expressed in the normal state associated with synapses and is believed to play a role in neural plasticity, learning and memory. Several studies have implicated alpha-synuclein with a central role in PD pathogenesis. The protein can aggregate to form insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polymeropoulos, et al., Science (1997) 276:2045-7). Over expression of alpha synuclein in transgenic mice (Masliah et al., Science (2000) 287:1265-9) and *Drosophila* (Feany et al., Nature (2000) 404:394-8) mimics several pathological aspects of Lewy body disease. In addition, it has been suggested that soluble oligomers of synuclein may be neurotoxic (Conway K A, et al., Proc Natl Acad Sci USA (2000) 97:571-576; Volles M J, Lansbury P T, Jr Biochemistry (2003) 42:7871-7878). The accumulation of alpha-synuclein with similar morphological and neurological alterations in species and animal models as diverse as humans, mice, and flies suggests that this molecule contributes to the development of Lewy body disease.

SUMMARY OF THE CLAIMED INVENTION

The invention provides antibodies comprising a mature humanized heavy chain variable region comprising the three Kabat CDRs of SEQ ID NO:11, and being at least 90% identical to SEQ ID NO:11, and a humanized light chain comprising the three Kabat CDRs of SEQ ID NO:4, and being at least 90% identical to SEQ ID NO:4. In some antibodies, the mature heavy chain variable region is at least 95%, 96%, 97%, 98%, or 99% identical to SEQ ID NO:11 and mature light chain variable region is at least 95%, 96%, 97%, 98%, or 99% identical to SEQ ID NO:4. In some antibodies position L36 (Kabat numbering) can be occupied by Y or F, position L83 (Kabat numbering) can be occupied by F or L, position H73 (Kabat numbering) can be occupied by N or D and position H93 (Kabat numbering) can be occupied by A or S. In some of such antibodies the amino acid sequence of the mature heavy chain variable region is otherwise that of SEQ ID NO:11 and the amino acid sequence of the mature light chain variable region is otherwise that of SEQ ID NO:4.

In some antibodies, the mature heavy chain variable region has an amino acid sequence designated SEQ ID NO:8 and the mature light chain variable region has an amino acid sequence designated SEQ ID NO:3. In some antibodies, the mature heavy chain variable region has an amino acid sequence designated SEQ ID NO:8 and the mature light chain variable region has an amino acid sequence designated SEQ ID NO:4. In some antibodies, the mature heavy chain variable region has an amino acid sequence designated SEQ ID NO:8 and the mature light chain variable region has an amino acid sequence designated SEQ ID NO:5. In some antibodies, the mature heavy chain variable region has an amino acid sequence designated SEQ ID NO:9 and the mature light chain variable region has an amino acid sequence designated SEQ ID NO:3. In some antibodies, the mature heavy chain variable region has an amino acid sequence designated SEQ ID NO:9 and the mature light chain variable region has an amino acid sequence designated SEQ ID NO:4. In some antibodies, the mature heavy chain variable region has an amino acid sequence designated SEQ ID NO:9 and the mature light chain variable region has an amino acid sequence designated SEQ ID NO:5. In some antibodies, the mature heavy chain variable region has an amino acid sequence designated SEQ ID NO:10 and the mature light chain variable region has an amino acid sequence designated SEQ ID NO:3. In some antibodies, the mature heavy chain variable region has an amino acid sequence designated SEQ ID NO:10 and the mature light chain variable region has an amino acid sequence designated SEQ ID NO:4. In some antibodies, the mature heavy chain variable region has an amino acid sequence designated SEQ ID NO:10 and the mature light chain variable region has an amino acid sequence designated SEQ ID NO:5. In some antibodies, the mature heavy chain variable region has an amino acid sequence designated SEQ ID NO:11 and the mature light chain variable region has an amino acid sequence designated SEQ ID NO:3. In some antibodies, the mature heavy chain variable region has an amino acid sequence designated SEQ ID NO:11 and the mature light chain variable region has an amino acid sequence designated SEQ ID NO:4. In some antibodies, the mature heavy chain variable region has an amino acid sequence designated SEQ ID NO:11 and the mature light chain variable region has an amino acid sequence designated SEQ ID NO:5.

The invention further provides an antibody comprising a humanized heavy chain comprising the three Kabat CDRs of SEQ ID NO:11 and a humanized light chain comprising the three CDRs of SEQ ID NO:4 provided that position L36 (Kabat numbering) is occupied by F or Y and/or position L83 (Kabat numbering) is occupied by L or F and/or position H73 (Kabat numbering) is occupied by D or N, and/or position H93 (Kabat numbering) is occupied by S or A. In some such antibodies, position L36 (Kabat numbering) is occupied by F and position H73 (Kabat numbering) is occupied by D, and position H93 (Kabat numbering) is occupied by S. In some such antibodies, position L36 is occupied by F. In some such antibodies, position L83 is occupied by L. In some such antibodies position H73 is occupied by D. In some such antibodies, position H93 is occupied by A. In some such antibodies, position L36 is occupied by F and position L83 is occupied by L. In some such antibodies, position L36 is occupied by F and position H73 is occupied by D. In some such antibodies, position L36 is occupied by F and position H93 is occupied by A. In some such antibodies, position L36 is occupied by F, position L83 is occupied by L and position H73 is occupied by D. In some such antibodies, position L36 is occupied by F, position L83 is occupied by L and position H93 is occupied by A. In some such antibodies, position L36 is occupied by F, position L83 is occupied by L, position 1173 is occupied by D and position H93 is occupied by A. In some such antibodies, residues at positions L36, L83, H73 and H93 (Kabat numbering) are occupied by amino acids as indicated in Table 1 is occupied by F and position H73 (Kabat numbering) is occupied by D, and position H93 (Kabat numbering) is occupied by A. In some such antibodies, position L36 (Kabat numbering) is occupied by F and position H93 (Kabat numbering) is occupied by S. In some such antibodies, position H73 (Kabat numbering) is occupied by D and position H93 (Kabat numbering) is occupied by S. In some such antibodies, position 1173 (Kabat numbering) is occupied by D and position 1193 (Kabat numbering) is occupied by A. In some such antibodies, position H93 (Kabat numbering) is occupied by S. In some such antibodies, position 1173 (Kabat numbering) is occupied by N. In some such antibodies, position L36 (Kabat numbering) is occupied by F, position L83 (Kabat numbering) is occupied by L, position H73 (Kabat numbering) is occupied by D, and position H93 (Kabat numbering) is occupied by S. In some such antibodies, position L36 (Kabat numbering) is occupied by F, position L83 (Kabat numbering) is occupied by L and position H93 (Kabat numbering) is occupied by S.

In any of the above antibodies, the mature heavy chain variable region can be fused to a heavy chain constant region and the mature light chain constant region can be fused to a light chain constant region.

In any of the above antibodies, the heavy chain constant region can be a mutant form of natural human constant region which has reduced binding to an Fcγ receptor relative to the natural human constant region.

In any of the above antibodies, the heavy chain constant region can be of human IgG1 isotype. In some antibodies the allotype is G1m3. In some antibodies, the allotype is G1m1.

The invention further provides a nucleic acid encoding any of the above-mentioned mature heavy chain variable regions and/or any of the above-mentioned mature light chain variable region, e.g., SEQ ID NO:15, 17, 18, 19, and 20.

The invention further provides a host cell comprising a vector comprising any of the nucleic acids described above.

The invention further provides a method of treating a patient having or at risk of a Lewy body disease, comprising administering to the patient an effective regime of any of the above-mentioned antibodies. In some methods, the disease is Parkinson's disease. In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of treating a patient having or at risk of synucleinopathy, comprising administering to the patient an effective regime of any of the above-mentioned antibodies. In some methods, the disease is Parkinson's disease. In some methods, the disease is REM sleep behavior disorder (RBD). In some methods, the disease is Dementia with Lewy Bodies (DLB) or multiple system atrophy (MSA). In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides methods of detecting Lewy bodies in a patient having or at risk of a Lewy body disease, comprising administering to the patient an effective amount of any of the above-mentioned antibodies, wherein the antibody binds to Lewy bodies and bound antibody is detected. In some methods, the disease is Parkinson's disease. In some methods, the disease is Dementia with Lewy Bodies (DLB) or multiple system atrophy (MSA). In some methods, the antibody is labeled.

The invention further provides a method of reducing Lewy body formation in a patient having or at risk of a Lewy body disease, comprising administering to the patient an effective amount of any of the above-mentioned antibodies. In some methods, the disease is Parkinson's disease. In some methods, the disease is Dementia with Lewy Bodies (DLB) or multiple system atrophy (MSA). In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of inhibiting synuclein aggregation or clearing Lewy bodies or synuclein aggregates in a patient having or at risk of a Lewy body disease, comprising administering to the patient an effective amount of any of the above-mentioned antibodies. In some methods, the disease is Parkinson's disease. In some methods, the disease is Dementia with Lewy Bodies (DLB) or multiple system atrophy (MSA). In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a pharmaceutical composition comprising any of the above-mentioned antibodies.

The invention further provides a method of producing an antibody, comprising culturing cells transformed with nucleic acids encoding the heavy and light chains of the antibody, so that the cell secrete the antibody; and purifying the antibody from cell culture media; wherein the antibody is any of the antibodies described above.

The invention further provides a method producing a cell line producing an antibody, comprising introducing a vector encoding heavy and light chains of an antibody and a selectable marker into cells; propagating the cells under conditions to select for cells having increased copy number of the vector; isolating single cells from the selected cell; and banking cells cloned from a single cell selected based on yield of antibody; wherein the antibody is any of the antibodies described above. Some such methods further comprises propagating the cells under selective conditions and screening for cell lines naturally expressing and secreting at least 100 mg/L/$10^6$ cells/24 h.

BRIEF DESCRIPTION OF THE FIGURES

FIG. 1 shows an alignment of the amino acid sequences of the parental murine mAb (referred to as m9E4) with the humanized 9E4 heavy chain mature variable region. 1791009Hu9E4VHFr (SEQ ID NO:7) is human acceptor $V_H$ sequence. CDR regions according to Kabat definition are underlined and in bold.

FIG. 2 shows an alignment of the amino acid sequences of the parental murine mAb (referred to as m9E4) with the humanized 9E4 light chain mature variable region. 63102889Hu9E4VLFr (SEQ ID NO:2) is human acceptor $V_L$ sequence. CDR regions according to Kabat definition are underlined and in bold.

FIG. 3 shows the results of passive immunotherapy with 9E4 on memory performance in probe portion of the Morris water maze test.

FIG. 4 shows the results of passive immunotherapy with 9E4 on speed and errors in the round beam test.

BRIEF DESCRIPTION OF THE SEQUENCES

Figure 5:
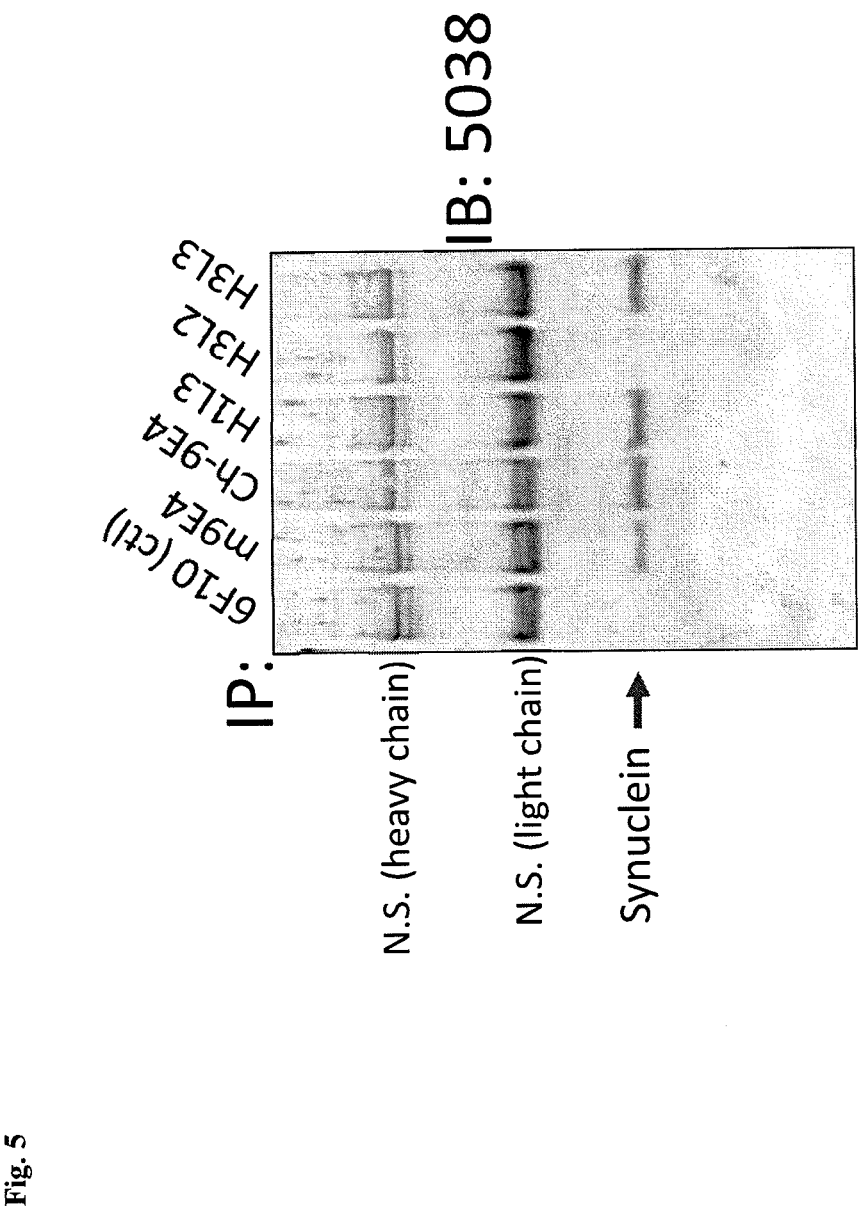
FIG. 5 shows immunoprecipitation of various versions of humanized 9E4 antibodies towards its antigen taken from diseased tissue. Ch9E4: chimeric 9E4; H1L3: Hu9E4VHv1-Hu9E4VLv3; H3L2: Hu9E4VHv3-Hu9E4VLv2; H3 L3: Hu9E4VHv3-Hu9E4VLv3; N.S.=non-specific.

SEQ ID NO:1 is the amino acid sequence of m9E4VL variable region.

SEQ ID NO:2 is the amino acid sequence of 63102889Hu9E4VLFr variable region.

SEQ ID NO:3 is the amino acid sequence of Hu9E4VLv1 variable region.

SEQ ID NO:4 is the amino acid sequence of Hu9E4VLv2 variable region.

SEQ ID NO:5 is the amino acid sequence of Hu9E4VLv3 variable region.

SEQ ID NO:6 is the amino acid sequence of m9E4VH variable region.

SEQ ID NO:7 is the amino acid sequence of 1791009Hu9E4VHFr variable region.

SEQ ID NO:8 is the amino acid sequence of Hu9E4VHv1 variable region.

SEQ ID NO:9 is the amino acid sequence of Hu9E4VHv2 variable region.

SEQ ID NO:10 is the amino acid sequence of Hu9E4VHv3 variable region.

SEQ ID NO:11 is the amino acid sequence of Hu9E4VHv4 variable region.

SEQ ID NO:12 is the amino acid sequence of natural human wild-type alpha-synuclein.

SEQ ID NO:13 is the amino acid sequence of humanized 9E4 light chain constant region, with Arginine at the N-terminus.

SEQ ID NO:14 is the amino acid sequence of humanized 9E4 heavy chain constant region.

SEQ ID NO:15 is the nucleotide sequence of Hu9E4VLv1 variable region.

SEQ ID NO:16 is the nucleotide sequence of Hu9E4VLv2 variable region.

SEQ ID NO:17 is the nucleotide sequence of Hu9E4VLv3 variable region.

SEQ ID NO:18 is the nucleotide sequence of Hu9E4VHv1 variable region.

SEQ ID NO:19 is the nucleotide sequence of Hu9E4VHv2 variable region.

SEQ ID NO:20 is the nucleotide sequence of Hu9E4VHv3 variable region.

SEQ ID NO:21 is the nucleotide sequence of Hu9E4VHv4 variable region.

SEQ ID NO:22 is the amino acid sequence of Hu9E4VL signal peptide.

SEQ ID NO:23 is the nucleotide sequence of Hu9E4VL signal peptide.

SEQ ID NO:24 is the amino acid sequence of Hu9E4VH signal peptide.

SEQ ID NO:25 is the nucleotide sequence of Hu9E4VH signal peptide.

SEQ ID NO:26 is the Hu9E4VL consensus amino acid sequence.

SEQ ID NO:27 is the Hu9E4VH consensus amino acid sequence.

SEQ ID NO:28 is the amino acid sequence of humanized 9E4 light chain constant region, without the Arginine at the N-terminus.

SEQ ID NO:29 is the amino acid sequence of the version 3 humanized 9E4 light chain comprising (a) a variable region and (b) a constant region with Arginine at the N-terminus.

SEQ ID NO:30 is the amino acid sequence of the version 3 humanized 9E4 light chain comprising (a) a variable region and (b) a constant region without the Arginine at the N-terminus.

SEQ ID NO:31 is the amino acid sequence of the version 3 humanized 9E4 heavy chain comprising a variable region and a constant region.

SEQ ID NO:32 is the amino acid sequence of the BIP version of humanized 9E4 heavy chain G1m3 allotype constant region.

Definitions

Monoclonal antibodies are typically provided in isolated form. This means that an antibody is typically at least 50% w/w pure of proteins and other macromolecules arising from its production or purification but does not exclude the possibility that the monoclonal antibody is combined with an excess of pharmaceutical acceptable carrier(s) or other vehicle intended to facilitate its use. Sometimes monoclonal antibodies are at least 60%, 70%, 80%, 90%, 95 or 99% w/w pure of proteins and other macromolecules from production or purification.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number (e.g., H83 means position 83 by Kabat numbering in the mature heavy chain variable region; likewise position L36 means position 36 by Kabat numbering in the mature light chain variable region).

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol. 148:1547-53 (1992)). In some bispecific antibodies, the two different heavy/light chain pairs include a humanized 9E4 heavy chain/light chain pair and a heavy chain/light chain pair specific for a different epitope on alpha synuclein than that bound by 9E4. Humanized antibodies are discussed generally below in Section IV B.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

A "patient" includes a human or other mammalian subject that receives either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range, and all subranges defined by integers within the range.

Unless otherwise apparent from the context, the term "about" encompasses values within the SEM of a stated value.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

Statistical significance means $p \leq 0.05$.

"Cognitive function" refers to mental processes such as any or all of attention, memory, producing and understanding language, solving problems, and making an interest in one's surroundings and self-care.

"Enhanced cognitive function" or "improved cognitive function" refers to improvement relative to a baseline, for example, diagnosis or initiation of treatment. "Decline of cognitive function" refers to a decrease in function relative to such a base line.

In animal model systems such as rat or mouse, cognitive function may be measured by methods using a maze in which subjects use spatial information (e.g, Morris water maze, Barnes circular maze, elevated radial arm maze, T maze and others), fear conditioning, active avoidance, illuminated open-field, dark activity meter, elevated plus-maze, two-compartment exploratory test or forced swimming test.

In humans, cognitive function can be measured by one or more of several standardized tests. Examples of a test or assay for cognitive function were described (Ruoppila, l. and Suutama, T. Scand. J. Soc. Med. Suppl. 53, 44-65, 1997) and include standardized psychometric tests (e.g. Wechsler Memory Scale, the Wechsler Adult Intelligence Scale, Raven's Standard Progressive Matrices, Schaie-Thurstone Adult Mental Abilities Test), neuropsychological tests (e.g. Luria-Nebraska), metacognitive self-evaluations (e.g. Metamemory Questionnaire), visual-spatial screening tests (e.g. Poppelreuter's Figures, Clock Recognition, Honeycomb Drawing and Cancellation), cognitive screening tests (e.g. Folstein's Mini Mental State Test) and reaction time tests. Other standard tests for cognitive performance include the Alzheimer's Disease Assessment Scale-cognitive subscale (ADAS-cog); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG), Stroop Test, Trail Making, Wechsler Digit Span, and the CogState computerized cognitive test. In addition, cognitive function may be measured using imaging techniques such as Positron Emission Tomography (PET), functional magnetic resonance imaging (fMRJ), Single Photon Emission Computed Tomography (SPECT), or any other imaging technique that allows one to measure brain function.

DETAILED DESCRIPTION

I. General

The invention provides humanized 9E4 antibodies. The antibodies are useful for treatment and diagnoses of a Lewy body disease.

II. Target Molecules

Natural human wildtype alpha-synuclein is a peptide of 140 amino acids having the following amino acid sequence:

```
                                           (SEQ ID NO: 12)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Ueda et al., Proc. Natl. Acad. Sci. USA (1993) 90:11282-6).; GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140.

Unless otherwise apparent from the context, reference to alpha-synuclein or its fragments includes the natural human wildtype amino acid sequences indicated above, and human allelic variants thereof, particularly those associated with Lewy body disease (e.g., E46K, A30P and A53T, with the first letter indicates the amino acid in SEQ ID NO:12, the number is the codon position in SEQ ID NO:12, and the second letter is the amino acid in the allelic variant). Such variants can optionally be present individually or in any combination in any of the aspect of the invention described below. The induced mutations E83Q, A90V, A76T, which enhance alpha synuclein aggregation, can also be present individually or in combination with each other and/or human allelic variants E46K, A30P and A53T.

III. Lewy Body Diseases

Lewy Body Diseases (LBD) are characterized by degeneration of the dopaminergic system, motor alterations, cognitive impairment, and formation of Lewy bodies (LBs). (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease and as multiple system atrophy (MSA; e.g., Olivopontocerebellar Atrophy, Striatonigral Degeneration and Shy-Drager Syndrome). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form mainly in the substantia nigra. Other Lewy Body diseases include Pure Autonomic Failure, Lewy body dysphagia, Incidental LBD, and Inherited LBD (e.g., mutations of the alpha-synuclein gene, PARK3 and PARK4).

IV. Antibodies of the Invention

A. Binding Specificity and Functional Properties

Humanized antibodies of the invention specifically bind to human alpha synuclein. The affinity of some humanized antibodies (i.e., Ka) is preferably within a factor of five or two of that of the mouse antibody 9E4. Some humanized antibodies have an affinity that is the same (within experimental error) or greater than that of the mouse 9E4 antibody. Preferred humanized antibodies bind to the same epitope and/or compete with the mouse antibody 9E4 for binding to human alpha synuclein.

In some antibodies, humanized 9E4 forms one arm of a bispecific antibody, the other arm of which is an antibody that binds to a receptor expressed on the blood brain barrier, such as an insulin receptor, an insulin-like growth factor (IGF) receptor, a leptin receptor, or a lipoprotein receptor, or preferably a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distributioin in the brain (see, e.g., Atwal. et al. Sci. Trans. Med. 3, 84ra43, 2011; Yu et al. Sci. Trans. Med. 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics), Fcab and Mab2 (F-star), Fc-engineered IgG1 (Xencor) or DuoBody (based on Fab arm exchange, Genmab).

B. Humanized Antibodies

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody variable region sequence, a composite of such sequences, a consensus sequence of human antibody sequences (e.g., light and heavy chain variable region consensus sequences of Kabat, 1991, supra), or a germline variable region sequence. A preferred acceptor sequence for the heavy chain is the human mature heavy chain variable region with NCBI accession code AAC50998 (GI: 1791009) or other mature heavy chain variable region derived from germline IGHV3-7'01 or IGHV3-7'02 (clones name V3-7 or VH3-11) (Glas et al., Clin Exp Immunol. 107:372-80, 1997) or a mature heavy chain variable region sequence incorporating one of these germ line sequences. For the light chain, a preferred acceptor sequence is the light chain mature variable region with NCBI accession code AAY33350 (GI: 63102889) or other mature light chain sequence derived from the germline IGKV1D-39 or IGKV1-39 (clone name O2 or O12) (Kramer et al., Eur J Immunol. 35:2131-45, 2005) or a light chain mature variable region sequence incorporating one of these germ line sequences. Thus, a humanized antibody of the invention is an antibody having three light chain and three heavy chain CDRs as defined by Kabat from the donor 9E4 antibody and mature variable region framework sequences and constant regions, if present, entirely or substantially from human antibody sequences. Likewise a humanized heavy chain is a heavy chain having three heavy chain CDRs as defined by Kabat from the heavy chain of the 9E4 antibody, and a mature heavy chain variable sequence and heavy chain constant region sequence, if present, entirely or substantially from human antibody heavy chain sequence. Likewise a humanized light chain is a light chain having three light chain CDRs as defined by Kabat from the light chain of the 9E4 antibody, and a mature light chain variable sequence and light chain constant region sequence, if present, entirely or substantially from human antibody light chain sequence. The mature variable region framework sequences of an antibody chain or the constant region sequence of an antibody chain are substantially from a human mature variable region framework sequence or human constant region sequence respectively when at least 85%, 90%, 95%, 96%, 97%, 98%, 99% or 100% of corresponding residues defined by Kabat are identical.

Certain amino acids from the human mature variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine mature variable region framework residue and a selected human mature variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region)
(4) mediates interaction between the heavy and light chains.

The invention provides humanized forms of the mouse 9E4 antibody including three exemplified humanized light chain mature variable regions (Hu9E4VLv1-v3; SEQ ID NOs:3-5) and four exemplified humanized heavy chain mature variable regions (Hu9E4VHv1-v4; SEQ ID NOs:8-11). SEQ ID NO:4 includes the three Kabat CDRs of the mouse 9E4 light chain and the mature variable region frameworks of AAY33350. SEQ ID NOS. 3 and 5 include backmutations as shown in Table 2. SEQ ID NO. 11 includes the three Kabat CDRs of mouse 9E4 and the mature variable region frameworks of AAC50998. SEQ ID NOs:8-10 include backmutations as shown in Table 3.

The invention provides variants of the humanized 9E4 antibody in which the humanized heavy chain mature variable region shows at least 90%, 95% or 99% identity to SEQ ID NOs:8-11 and the humanized light chain mature variable region shows at least 90, 95 or 99% sequence identity to SEQ ID NOs:3-5, but in which any variation from the designated SEQ ID NO. occurs in a mature variable region framework rather than a Kabat CDR. In some such antibodies, position L36 is occupied by Y or F, and/or position L83 is occupied by F or L, and/or position H73 is occupied by N or D and/or position H93 is occupied by A or S (all positions here, as elsewhere, in this application are by Kabat numbering). In some such antibodies, some or all of the back-mutations in Hu9E4VLv1-v3 and Hu9E4VHv1-v4 are retained. In other words, one or both of heavy chain positions H73 and H93 is occupied by D and A respectively. Likewise in some antibodies one or both of light chain positions L36 and L83 is occupied by F and L respectively. In some antibodies, 1, 2, 3 or all four of positions H73, H93, L36 and L83 is/are occupied by D, A, F and L respectively. In some antibodies, 0, 1, or 2 positions are changed in the heavy chain mature variable region framework relative to SEQ ID NO:11, and 0, 1, or 2 positions are change in the light chain mature variable region framework relative to SEQ ID NO:4.

Some antibodies comprise a humanized heavy chain comprising the three Kabat CDRs of SEQ ID NO:11 and a humanized light chain comprising the three Kabat CDRs of SEQ ID NO:4 provided that position L36 (Kabat numbering) is occupied by F or Y and/or position L83 (Kabat numbering) is occupied by L or F and/or position H73 (Kabat numbering) is occupied by D or N, and/or position H93 (Kabat numbering) is occupied by S or A. In some such antibodies, position L36 (Kabat numbering) is occupied by F. In some such antibodies, position L36 (Kabat numbering) is occupied by F and position L83 (Kabat numbering) is occupied by L. In some such antibodies, position L36 (Kabat numbering) is occupied by F and position H73 (Kabat numbering) is occupied by D. In some such antibodies, position L36 (Kabat numbering) is occupied by F and position H93 (Kabat numbering) is occupied by S. In some such antibodies, position L36 (Kabat numbering) is occupied by F and position H93 (Kabat numbering) is occupied by A. In some such antibodies, position L36 (Kabat numbering) is occupied by F, position L83 (Kabat numbering) is occupied by L, and position H73 (Kabat numbering) is occupied by D. In some such antibodies, position L36 (Kabat numbering) is occupied by F, position L83 (Kabat numbering) is occupied by L, and position H93 (Kabat numbering) is occupied by S. In some such antibodies, position L36 (Kabat numbering) is occupied by F, position L83 (Kabat numbering) is occupied by L, and position H93 (Kabat numbering) is occupied by A. In some such antibodies, position L36 (Kabat numbering) is occupied by F, position H73 (Kabat numbering) is occupied by D, and position H93 (Kabat numbering) is occupied by S. In some such antibodies, position L36 (Kabat numbering) is occupied by F, position L83 is occupied by F, position H73 (Kabat numbering) is occupied by D, and position H93 (Kabat numbering) is occupied by S. In some such antibodies, position L36 (Kabat numbering) is occupied by F, position H73 (Kabat numbering) is occupied by D, and position H93 (Kabat numbering) is occupied by A. In some such antibodies, position L36 (Kabat numbering) is occupied by F, position L83 (Kabat numbering) is occupied by L, position H73 (Kabat numbering) is occupied by D, and position H93 (Kabat numbering) is occupied by S. In some such antibodies, position L36 (Kabat numbering) is occupied by F, position L83 (Kabat numbering) is occupied by L, position H73 (Kabat numbering) is occupied by D, and position H93 (Kabat numbering) is occupied by A. In some such antibodies, position L83 (Kabat numbering) is occupied by L. In some such antibodies, position L83 (Kabat numbering) is occupied by L and position H73 (Kabat numbering) is occupied by D. In some such antibodies, position L83 (Kabat numbering) is occupied by L and position H93 (Kabat numbering) is occupied by S. In some such antibodies, position L83 (Kabat numbering) is occupied by L and position H93 (Kabat numbering) is occupied by A. In some such antibodies, position L83 (Kabat numbering) is occupied by L, position H73 (Kabat numbering) is occupied by D, and position H93 (Kabat numbering) is occupied by S. In some such antibodies, position L83 (Kabat numbering) is occupied by L, position H73 (Kabat numbering) is occupied by D, and position H93 (Kabat numbering) is occupied by A. In some such antibodies, position H73 (Kabat numbering) is occupied by D. In some such antibodies, position H73 (Kabat numbering) is occupied by D and position H93 (Kabat numbering) is occupied by S. In some such antibodies, position H73 (Kabat numbering) is occupied by D and position H93 (Kabat numbering) is occupied by A. In some such antibodies, position H93 (Kabat numbering) is occupied by S. In some such antibodies, position H93 (Kabat numbering) is occupied by A. In some such antibodies, position L36 is occupied by Y, position L83 is occupied by F, position H73 is occupied by N and position H93 is occupied by S. Some exemplary antibodies with desirable residues at positions L36, L83, H73, and H93 and combinations thereof are listed in Table 1 below:

TABLE 1

Exemplary antibodies with desirable residues at positions L36, L83, H73, and H93 (Kabat numbering).

| Exemplary Antibody | L36 | L83 | H73 | H93 |
|---|---|---|---|---|
| 1 | F | F | N | A |
| 2 | F | L | N | A |
| 3 | F | F | D | A |
| 4 | F | F | N | S |
| 5 (version 3) | F | L | D | A |
| 6 | F | L | N | S |
| 7 (version 1) | F | F | D | S |
| 8 | F | L | D | S |
| 9 | Y | L | N | A |
| 10 | Y | L | D | A |
| 11 | Y | L | N | S |
| 12 | Y | L | D | S |
| 13 | Y | F | D | A |
| 14 | Y | F | D | S |
| 15 (version 2) | Y | F | N | S |

In some antibodies, the heavy chain mature variable region has an amino acid sequence designated SEQ ID NO:10. In some antibodies, the light chain mature variable region has an amino acid sequence designated SEQ ID NO:5 or SEQ ID NO:3. In some such antibodies, the heavy chain mature variable region has an amino acid sequence designated SEQ ID NO:10, and the light chain mature variable region has an amino acid sequence designated SEQ ID NO:5 or SEQ ID NO:3. In some such antibodies, the heavy chain mature variable region has an amino acid sequence designated SEQ ID NO:10, and the light chain mature variable region has an amino acid sequence designated SEQ ID NO:5.

Other amino acid substitutions can be made in the mature variable region framework, for example, in residues not in contact with the CDRs. Often the replacements made in the variant humanized sequences are conservative with respect to the replaced amino acids. In some antibodies, replacements relative to Hu9E4VLv1-v3 and Hu9E4VHv1-v4 (whether or not conservative) have no substantial effect on the binding affinity or potency of the resultant antibody relative to Hu9E4VLv1-v3 and Hu9E4VHv1-v4, that is, its ability to bind human alpha synuclein.

Variants typically differ from the heavy and light chain mature variable region sequences of Hu9E4VLv1-v3 and Hu9E4VHv1-v4 by a small number (e.g., typically no more than 1, 2, 3, 5 or 10 in either the light chain or heavy chain mature variable region framework, or both) of replacements, deletions or insertions.

C. Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO:13. Some such light chain kappa constant regions can be encoded by a nucleic acid sequence. The N-terminal arginine of SEQ ID NO:13 can be omitted, in which case light chain kappa constant region has the amino acid sequence of SEQ ID NO:28. Some such light chain kappa constant regions can be encoded by a nucleic acid sequence. An exemplary human IgG1 heavy chain constant region has the amino acid sequence of SEQ ID NO:14 (with or without the C-terminal lysine). Some such heavy chain constant regions can be encoded by a nucleic acid sequence. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence of SEQ ID NO:32. Yet another heavy chain constant region has the amino acid sequence of SEQ ID NO:32 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821).

D. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., J. Immunol. 148:1149 (1992).

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carboydrateoligosaccharide mapping, mass spectrometery, and bining assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, *Protein Purification* (Springer-Verlag, N.Y., 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

V. Nucleic Acids

The invention further provides nucleic acids encoding any of the heavy and light chains described above. Typically, the nucleic acids also encode a signal peptide fused to the mature heavy and light chains (e.g., signal peptides having amino acid sequences of SEQ ID NOS: 22 and 24 that can be encoded by SEQ ID NOS: 23 and 25). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

VI. Therapeutic Applications

The invention provides several methods of treating or effecting prophylaxis of Lewy Body disease in patients suffering from or at risk of such disease. Patients amenable to treatment include individuals at risk of disease of a LBD but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/ gain). Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHLI, and CYP2D6 genes; particularly mutations at positions 30 and 53 of the alpha-synuclein gene. Individuals presently suffering from Parkinson's disease can be recognized from its clinical manifestations including resting tremor, muscular rigidity, bradykinesia and postural instability.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of alpha-synuclein peptide) over time. If the response falls, a booster dosage is indicated.

Antibodies can be used for treating or effecting prophylaxis of Lewy Body disease in patients by administration under conditions that generate a beneficial therapeutic response in a patient (e.g., reduction of neuritic and/or axonal alpha synuclein aggregates, reduction of neuritic dystrophy, improving cognitive function, and/or reversing, treating or preventing cognitive decline) in the patient. In some methods, the areas of neuritic dystrophy in the neuropil of neocortex and/or basal ganglia can be reduced by on average at least 10%, 20%, 30%, or 40% in treated patients compared with a control population.

Cognitive impairment, progressive decline in cognitive function, changes in brain morphology, and changes in cerebrovascular function are commonly observed in patients suffering from or at risk of Lewy Body disease. Administration of the present antibodies can inhibit or delay decline of cognitive function in such patients.

The invention also provides methods of preserving or increasing synaptic density and/or dentritic density. An index of changes in synaptic or dentritic density can be measured by markers of synapse formation (synaptophysin) and/or dendrites (MAP2). In some methods, the synaptic or dentritic density can be restored to the level of synaptic or dentritic density in a healthy subject. In some methods, the mean level of synaptic or dentritic density in treated patients can be elevated by 5%, 10%, 15%, 20%, 25%, 30% or more as compared to a population of untreated control patients.

VII. Pharmaceutical Compositions and Methods of Treatment

In prophylactic applications, an antibody or agent for inducing an antibody or a pharmaceutical composition the same is administered to a patient susceptible to, or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha synuclein and truncated fragments in the brain, and/or inhibit or delay its toxic effects and/or inhibit/or delay development of behavioral deficits. In therapeutic applications, an antibody or agent to induce an antibody is administered to a patient suspected of, or already suffering from a Lewy body disease in a regime (dose, frequency and route of administration) effective to ameliorate or at least inhibit further deterioration of at least one sign or symptom of the disease. In some therapeutic applications, the regime is effective to reduce or at least inhibit further increase of levels of alpha synuclein and truncated fragments, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses vary depending upon many different factors, including means of administration, target site, physiological state of the patient including type of Lewy body disease, whether the patient is an ApoE carrier, whether the patient is human or an animal, other medications administered, and whether treatment is prophylactic or therapeutic.

An exemplary dosage range for antibodies is from about 0.01 to 5 mg/kg, and more usually 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Antibodies can be administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Some routes for administration of antibodies are intravenous and subcutaneous. This type of injection is most typically performed in the arm or leg muscles. In some methods, agents are injected directly into a particular tissue where deposits have accumulated, for example intracranial injection.

Pharmaceutical compositions for parenteral administration are can be sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Parkinson's disease, immunotherapy against alpha synuclein WO/2008/103472, Levodopa, dopamine agonists, COMT inhibitors, MAO-B inhibitors, Amantadine, or anticholinergic agents can be used in combination with the present regimes.

VIII. Other Applications

The antibodies described above can be used for detecting alpha-synuclein in the context of clinical diagnosis or treatment or in research. The antibodies can also be sold as research reagents for laboratory research in detecting cells bearing alpha-synuclein and their response to various stimuli. In such uses, monoclonal antibodies can be labeled with fluorescent molecules, spin-labeled molecules, enzymes or radioisotopes, and can be provided in the form of kit with all the necessary reagents to perform the assay for alpha-synuclein. The antibodies can also be used to purify alpha-synuclein, e.g., by affinity chromatography.

The antibodies can be used for detecting LBs in a patient. Such methods are useful to diagnose or confirm diagnosis of PD, or other disease associated with the presence of LBs in the brain, or susceptibility thereto. For example, the methods can be used on a patient presenting with symptoms of dementia. If the patient has LBs, then the patient is likely suffering from a Lewy body disease, such as Parkinson's disease. The methods can also be used on asymptomatic patients. Presence of Lewy bodies or other abnormal deposits of alpha-synuclein indicates susceptibility to future symptomatic disease. The methods are also useful for monitoring disease progression and/or response to treatment in patients who have been previously diagnosed with a Lewy body disease.

The methods can be performed by administering an antibody and then detecting the antibody after it has bound. If desired, the clearing response can be avoided by using an antibody fragment lacking a full-length constant region, such as a Fab. In some methods, the same antibody can serve as both a treatment and diagnostic reagent.

For diagnosis (e.g., in vivo imaging), the antibodies can be administered by intravenous injection into the body of the patient, or directly into the brain by intracranial injection or by drilling a hole through the skull. The dosage of reagent should be within the same ranges as for treatment methods. Typically, the antibody is labeled, although in some methods, the antibody is unlabelled and a secondary labeling agent is used to bind to the antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labeled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

The antibodies can be used to generate anti-idiotype antibodies. (see, e.g., Greenspan & Bona, FASEB J. 7(5): 437-444, 1989; and Nissinoff, J. Immunol. 147:2429-2438, 1991). Such anti-idiotype antibodies can be utilized in pharmacokinetics, pharmacodynamics, biodistribution studies as well as in studies of clinical human-anti-human antibody (HAHA) responses in individuals treated with the antibodies. For example, anti-idiotypic antibodies bind specifically the variable region of humanized 9E4 antibodies and therefore can be used to detect humanized 9E4 antibodies in pharmacokinetic studies and help to quantify human-anti-human antibody (HAHA) responses in treated individuals.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example I. Design of Humanized 9E4 Antibodies

The starting point or donor antibody for humanization is the mouse antibody 9E4 produced by the hybridoma having ATCC Accession No. PTA-8221 and described in U.S. patent application Ser. No. 11/710,248 (publication number US2009/0208487). The variable kappa (Vκ) of 9E4 belongs to mouse Kabat subgroup 1 which corresponds to human Kabat subgroup 1. The variable heavy (Vh) of 9E4 belongs to mouse Kabat subgroup 3d which corresponds to human Kabat subgroup 3 (Kabat et al., Sequences of Proteins of Immunological Interest, Fifth Edition. NIH Publication No. 91-3242, 1991). Kabat numbering is used throughout in this Example.

The 17-residue CDR-L1 belongs to canonical class 3, the 7-residue CDR-L2 belongs to class 1, and the 9-residue CDR-L3 belongs to class 1 in Vκ (Martin & Thornton, J Mol Biol. 263:800-15, 1996). The 5-residue CDR-H1 belongs to class 1, and the 17-residue CDR-H2 belongs to class 2 (Martin & Thornton, J Mol Biol. 263:800-15, 1996). CDR-H3 has no canonical classes, but the 7 residue loop probably has a kinked base according to the rules of Shirai et al. (FEBS Lett. 455:188-97, 1999).

A search was made over the protein sequences in the PDB database (Deshpande et al., Nucleic Acids Res. 33: D233-7, 2005) to find structures which would provide a rough structural model of 9E4. The crystal structure of dimeric antibody X836 (pdb code 3MBX) (Teplyakov et al, Mol Immunol., 47(14):2422-6, 2010) was chosen for the Vκ structure since it had good resolution (1.6 A) and overall sequence similarity to 9E4 Vκ, retaining the same canonical structures for the loops. 1H3P (Pizarro et al., FEBS Lett. 509:463-8, 2001) was used for the Vh structure. It had good overall sequence similarity and reasonable resolution (2.6 A), but also had the same length CDR-H3 with a kinked base. In addition, CDRs-H1 and H2 had the same canonical structures as 9E4 Vh. DeepView/Swiss-PdvViewer 3.7 (SP5) (Guex and Peitsch, Electrophoresis 18: 2714-2723, 1997) was used structure modeling.

A search of the non-redundant protein sequence database from NCBI allowed selection of suitable human frameworks into which to graft the murine CDRs. For Vκ, a human kappa light chain with NCBI accession code AAY33350 (GI:63102889) (Kramer et al., Eur J Immunol. 35:2131-45, 2005) was chosen. It has the same canonical classes for CDR-L2 and L3 as 9E4, and belongs to human germline IGKV1D-39 or IGKV1-39 (clone name 02 or 012) according to IMGT convention. It is a member of Kabat human kappa subgroup 1. For Vh, human Ig heavy chain with NCBI accession code AAC50998 (GI:1791009) (Glas et al., Clin Exp Immunol. 107:372-80, 1997) was chosen, again with the same canonical classes as 9E4 and belonging to human germline IGHV3-7'01 or IGHV3-7'02 (clones name V3-7 or VH3-11). It is a member of Kabat human heavy subgroup 3.

The following positions differing between the human acceptor and mouse donor variable region frameworks were identified as being candidates for backmutation. H73 is on the edge of the antigen binding site and interacts with CDR-H2. H93 is an interface residue that lies beneath the CDR-H1 and H3 loops. L36 is a Vκ/Vh interface residue. L83 is in close proximity to the constant domain. In 9E4, L83 is a leucine, whereas in human framework, L83 is a larger amino acid phenylalanine.

Three humanized heavy chains and three humanized light chains are made incorporating back mutations at different permutations of these positions (FIGS. 1A, B, sequence alignment, and Tables 2-3).

TABLE 2

$V_H$ Backmutations

| $V_H$ variant | $V_H$ exon acceptor sequence | donor framework residues |
|---|---|---|
| Hu9E4VHv1 | NCBI accession code AAC50998 | H73, H93 |

TABLE 2-continued $V_H$ Backmutations

| $V_H$ variant | $V_H$ exon acceptor sequence | donor framework residues |
|---|---|---|
| Hu9E4VHv2 | NCBI accession code AAC50998 | H93 |
| Hu9E4VHv3 | NCBI accession code AAC50998 | H73 |

TABLE 3

$V_L$ Backmutations

| $V_L$ variant | $V_L$ exon acceptor sequence | donor framework residues |
|---|---|---|
| Hu9E4VLv1 | NCBI accession code AAY33350 | L36 |
| Hu9E4VLv2 | NCBI accession code AAY33350 | None |
| Hu9E4VLv3 | NCBI accession code AAY33350 | L36, L83 |

```
>9E4Vκ Version1
                                       (SEQ ID NO: 3)
DIQMTQSPSSLSASVGDRVTITCKSIQTLLYSSNQKNYLAWFQQK

PGKAPKLLIYWASIRKSGVPSRFSGSGSGTDFTLTISSLQPEDFA

TYYCQQYYSYPLTFGGGTKLEIK

>9E4Vκ Version2
                                       (SEQ ID NO: 4)
DIQMTQSPSSLSASVGDRVTITCKSIQTLLYSSNQKNYLAWYQQK

PGKAPKLLIYWASIRKSGVPSRFSGSGSGTDFTLTISSLQPEDFA

TYYCQQYYSYPLTFGGGTKLEIK

>9E4Vκ Version3
                                       (SEQ ID NO: 5)
DIQMTQSPSSLSASVGDRVTITCKSIQTLLYSSNQKNYLAWFQQK

PGKAPKLLIYWASIRKSGVPSRFSGSGSGTDFTLTISSLQPEDLA

TYYCQQYYSYPLTFGGGTKLEIK

>9E4vh Version1
                                       (SEQ ID NO: 8)
EVQLVESGGGLVQPGGSLRLSCAASGFTFSNYGMSWVRQAPGKGL

EWVASISSGGGSTYYPDNVKGRFTISRDDAKNSLYLQMNSLRAED

TAVYYCSRGGAGIDYWGQGTLVTVSS

>9E4vh Version2
                                       (SEQ ID NO: 9)
EVQLVESGGGLVQPGGSLRLSCAASGFTFSNYGMSWVRQAPGKGL

EWVASISSGGGSTYYPDNVKGRFTISRDNAKNSLYLQMNSLRAED

TAVYYCSRGGAGIDYWGQGTLVTVSS

>9E4vh Version3
                                       (SEQ ID NO: 10)
EVQLVESGGGLVQPGGSLRLSCAASGFTFSNYGMSWVRQAPGKGL

EWVASISSGGGSTYYPDNVKGRFTISRDDAKNSLYLQMNSLRAED

TAVYYCARGGAGIDYWGQGTLVTVSS
```

Kabat numbering for AAY33350 light chain and AAC50998 heavy chain are listed below:

| Kabat numbering for AAY33350 light chain: | | | | | | | | |
|---|---|---|---|---|---|---|---|---|
| L1 D | L2 I | L3 Q | L4 M | L5 T | L6 Q | L7 S | L8 P | L9 S |
| L10 S | L11 L | L12 S | L13 A | L14 S | L15 V | L16 G | L17 D | L18 R |
| L19 V | L20 T | L21 I | L22 T | L23 C | L24 R | L25 A | L26 S | L27 Q |
| L28 S | L29 I | L30 S | L31 S | L32 Y | L33 L | L34 N | L35 W | L36 Y |
| L37 Q | L38 Q | L39 K | L40 P | L41 G | L42 K | L43 A | L44 P | L45 K |
| L46 L | L47 L | L48 I | L49 Y | L50 A | L51 A | L52 S | L53 S | L54 L |
| L55 Q | L56 S | L57 G | L58 V | L59 P | L60 S | L61 R | L62 F | L63 S |
| L64 G | L65 S | L66 G | L67 S | L68 G | L69 T | L70 D | L71 F | L72 T |
| L73 L | L74 T | L75 I | L76 S | L77 S | L78 L | L79 Q | L80 P | L81 E |
| L82 D | L83 F | L84 A | L85 T | L86 Y | L87 Y | L88 C | L89 Q | L90 Q |
| L91 S | L92 Y | L93 S | L94 T | L95 P | L96 L | L97 T | L98 F | L99 G |
| L100 G | L101 G | L102 T | L103 K | L104 L | L105 E | L106 I | L107 K | L108 — |
| L109 — | L110 — | L111 — | | | | | | |

| Kabat numbering for AAC50998 heavy chain: | | | | | | | | |
|---|---|---|---|---|---|---|---|---|
| H1 E | H2 V | H3 Q | H4 L | H5 V | H6 E | H7 S | H8 G | H9 G |
| H10 G | H11 L | H12 V | H13 Q | H14 P | H15 G | H16 G | H17 S | H18 L |
| H19 R | H20 L | H21 S | H22 C | H23 A | H24 A | H25 S | H26 G | H27 F |
| H28 T | H29 F | H30 S | H31 S | H32 Y | H33 W | H34 M | H35 H | H36 W |
| H37 V | H38 R | H39 Q | H40 A | H41 P | H42 G | H43 K | H44 G | H45 L |
| H46 E | H47 W | H48 V | H49 A | H50 N | H51 I | H52 K | H52A Q | H53 D |
| H54 G | H55 S | H56 E | H57 K | H58 Y | H59 Y | H60 V | H61 D | H62 S |
| H63 V | H64 K | H65 G | H66 R | H67 F | H68 T | H69 I | H70 S | H71 R |
| H72 D | H73 N | H74 A | H75 K | H76 N | H77 S | H78 L | H79 Y | H80 L |
| H81 Q | H82 M | H82A N | H82B S | H82C L | H83 R | H84 A | H85 E | H86 D |
| H87 T | H88 A | H89 V | H90 Y | H91 Y | H92 C | H93 A | H94 R | H95 G |
| H96 S | H97 S | H98 D | H99 M | H100 — | H101 D | H102 Y | H103 W | H104 G |
| H105 Q | H106 G | H107 T | H108 L | H109 V | H110 T | H111 V | H112 S | H113 S |
| H114 — | | | | | | | | |

Kabat number of other heavy and light chain variable regions can be determined by alignment with corresponding residues assigned the same number or using commercially available software.

TABLE 4

Kabat numbering of preferred framework residues for backmutation in humanized 9E4 antibodies

| | AAY33350 light chain | AAC50998 heavy chain | Mouse 9E4 | Humanized 9E4 v1 | Humanized 9E4 v2 | Humanized 9E4 v3 | Humanized 9E4 v4 (heavy chain) |
|---|---|---|---|---|---|---|---|
| L36 | Y | — | F | F | Y | F | — |
| L83 | F | — | L | F | F | L | — |
| H73 | — | N | D | D | N | D | N |
| H93 | — | A | S | S | S | A | A |

Example II. Passive Immunization with α-Synuclein Antibodies

The goal of this experiment is to determine effectiveness of α-synuclein antibodies in in vitro and in vivo studies as well as behavioral assays. We used α-synuclein transgenic (Line 61), α-synuclein knockout and wildtype female mice, 3-4 months old at initiation and n=14/group. Antibodies tested included 9E4 (IgG1, epitope: amino acids 118-126 of alpha synuclein), 5C1 (IgG1, epitope: amino acids 118-126 of alpha synuclein, c-linker), 5D12, IgG2 (SN118-126), 1H7, IgG1 (SN 91-99) and an IgG1 control antibody 27-1. Mice received a dosage of 10 mg/kg over a 5 month period, for a total of 21 injections. In addition, the animals were injected with lentivirus (LV) expressing human α-synuclein (wt) by unilateral introduction of human α-synuclein (wt) into the hippocampus.

Readout antibodies include those from Chemicon (epitope: full-length alpha synuclein), Millipore (epitope: full-length alpha synuclein), and Neotope, ELADW 105 (epitope: amino acids 121-124 of full-length alpha synuclein).

Endpoints:

Antibody titers were measured during the in life phase. Behavioral assays include Morris Water Maze test (MWW) and horizontal beam test. The round beam test is a test of motor balance, coordination and gait conducted using two beams of varying diameter. Beam A is the larger diameter (easier, considered the training beam) and Beam D is the smaller diameter (more difficult, considered the testing beam). Data is presented as "errors" (number of slips/10 cm) and "speed" (time taken to travel 10 cm/sec). Water maze performance was carried out at weeks 10 and termination. The following neuropathology measurements were taken: alpha synuclein aggregation, synaptophysin, and MAP2. The following biochemistry measurements were taken: alpha synuclein, PSD95, synaptophysin. Selected multilabeling and confocal labeling were carried out using synaptic, neuronal and glial markers.

The results showed that all antibodies, except 5D12, produced significant reduction in α-syn accumulation and preservation of synaptic and dendritic densities, as well as positive outcomes in MWM performance. The 9E4 antibody is effective in in vitro and in vivo studies as well as behavioral assays. Readouts indicate antibody may reduce neuritic/axonal alpha synuclein aggregates.

Behavioral Results:

The 9E4 antibody improved water maze performance in α-synuclein transgenic mice (FIGS. 3-4). In contrast, the 5D12 antibody did not improve water maze performance in α-synuclein transgenic mice (FIG. 4). The 9E4 and 1H7 antibodies improved performance on the beam test as measured both by speed and errors, whereas the 5D12 and 5C1 antibodies did not (FIG. 4).

Neuropathology Results:

The 9E4, 1H7 and 5C1 antibodies reduced ELADW-105 positive neuritic dystrophy, whereas the 5D12 antibody did not. In alpha synuclein transgenic mice, the 9E4 antibody reduced the area of neuropil by 43% in neocortex and by 40% in basal ganglia as compared to control. The 9E4 antibody also preserved synaptophysin and MAP2 in neocortex and basal ganglia.

Example III. Immunoprecipitation

Immunoprecipitation was performed to test the binding efficacy of various versions of humanized 9E4 antibodies towards its antigen taken from diseased tissue (FIG. 5). 150 µg of Tris-soluble brain lysates from Dementia with Lewy Body brains were immunoprecipitated with 5 µg of each indicated antibody using Protein G magnetic beads (New England Biolabs). Samples were washed 5 times with PBS/350 mM NaCl/0.5% NP-40, boiled, and the resulting samples resolved by SDS-PAGE. After blotting, membranes were incubated with Ab5038 (Millipore), a polyclonal antibody that detects total synuclein. The experiment was repeated three times to confirm accuracy.

Example IV. Western Blot

Figure 6:
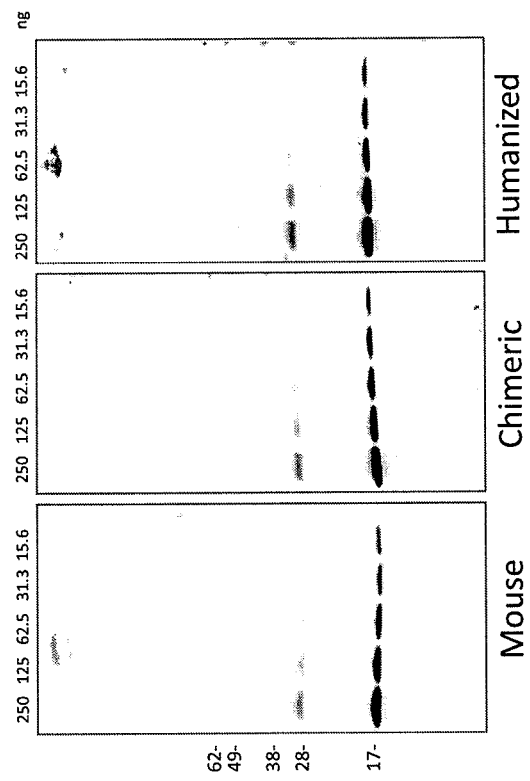
FIG. 6 shows Western blotting of recombinant human synuclein with mouse, chimeric and humanized 9E4 antibodies.

Western blotting of recombinant human synuclein with mouse, chimeric and humanized 9E4 antibodies is shown in FIG. 6. Antibody dilution curves were apparently similar for mouse, chimeric and humanized 9E4 antibodies. All antibodies detected a band at 28 KDa and a second band at 49 kDa. The 49 kDa band is likely a multimer of synuclein.

Indicated amounts of recombinant, bacterially-expressed human wild-type synuclein were resolved by SDS-PAGE, and blotted with identical amounts of the indicated form of 9E4. After washing, species-appropriate goat polyclonal antibodies conjugated to the IRDye-800 fluorophor were applied, and the blot was washed. Exposure times were identical for the different antibodies.

DEPOSIT

The following hybridoma has been deposited under the provisions of the Budapest Treaty with the American Type Culture Collection (ATCC, P.O. Box 1549, Manassas, Va. 20108) on the date indicated. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

| Monoclonal antibody | Cell Line | Epitope/Specificity | Isotype | Date of Deposit | Accession No. |
|---|---|---|---|---|---|
| 9E4 | JH17.9E4.3.37.1.14.2 | alpha-synuclein residues 118-126 | IgG1 κ | Feb. 26, 2007 | PTA-8221 |

What is claimed is:

1. An antibody comprising a mature heavy chain variable region comprising the three Kabat CDRs of SEQ ID NO:11, and being at least 90% identical to SEQ ID NO:11, and a light chain comprising the three Kabat CDRs of SEQ ID NO:4, and being at least 90% identical to SEQ ID NO:4.

2. The antibody of claim 1, wherein the mature heavy chain variable region is at least 95% identical to SEQ ID NO:11 and mature light chain variable region is at least 95% identical to SEQ ID NO:4.

3. The antibody of claim 1, wherein the mature heavy chain variable region has an amino acid sequence at least 98% identical to SEQ ID NO:11 and the mature light chain variable region has an amino acid sequence at least 95% identical to SEQ ID NO:4.

4. The antibody of claim 1, wherein the mature heavy chain variable region has an amino acid sequence at least 99% identical to SEQ ID NO:11 and the mature light chain variable region has an amino acid sequence at least 95% identical to SEQ ID NO:4.

5. The antibody of claim 1, wherein the mature heavy chain variable region has the amino acid sequence of SEQ ID NO:11 and the mature light chain variable region has an amino acid sequence at least 95% identical to SEQ ID NO:4.

6. The antibody of claim 1, wherein the mature heavy chain variable region has an amino acid sequence at least 95% identical to SEQ ID NO:11 and the mature light chain variable region has an amino acid sequence at least 98% identical to SEQ ID NO:4.

7. The antibody of claim 1, wherein the mature heavy chain variable region has an amino acid sequence at least 95% identical to SEQ ID NO:11 and the mature light chain variable region has an amino acid sequence at least 99% identical to SEQ ID NO:4.

8. The antibody of claim 1, wherein the mature heavy chain variable region has an amino acid sequence at least 95% identical to SEQ ID NO:11 and the mature light chain variable region has an amino acid sequence designated SEQ ID NO:4.

9. The antibody of claim 1, wherein the mature heavy chain variable region has an amino acid sequence at least 98% identical to SEQ ID NO:11 and the mature light chain variable region has an amino acid sequence at least 98% identical to SEQ ID NO:4.

10. The antibody of claim 1, wherein the mature heavy chain variable region has an amino acid sequence at least 99% identical to SEQ ID NO:11 and the mature light chain variable region has an amino acid sequence at least 99% identical to SEQ ID NO:4.

11. The antibody of claim 1, provided that position L36 (Kabat numbering) is occupied by F.

12. The antibody of claim 1, provided that position L83 (Kabat numbering) is occupied by L.

13. The antibody of claim 1, provided that position H73 (Kabat numbering) is occupied by D.

14. The antibody of claim 1, provided that position H93 (Kabat numbering) is occupied by S.

15. The antibody of claim 1, provided that position H93 (Kabat numbering) is occupied by A.

16. The antibody of claim 1, wherein the mature heavy chain variable region has an amino acid sequence designated SEQ ID NO:8 and the mature light chain variable region has an amino acid sequence designated SEQ ID NO:3.

17. The antibody of claim 1, wherein the mature heavy chain variable region has an amino acid sequence designated SEQ ID NO:8 and the mature light chain variable region has an amino acid sequence designated SEQ ID NO:4.

18. The antibody of claim 1, wherein the mature heavy chain variable region has an amino acid sequence designated SEQ ID NO:8 and the mature light chain variable region has an amino acid sequence designated SEQ ID NO:5.

19. The antibody of claim 1, wherein the mature heavy chain variable region has an amino acid sequence designated SEQ ID NO:9 and the mature light chain variable region has an amino acid sequence designated SEQ ID NO:3.

20. The antibody of claim 1, wherein the mature heavy chain variable region has an amino acid sequence designated SEQ ID NO:9 and the mature light chain variable region has an amino acid sequence designated SEQ ID NO:4.

21. The antibody of claim 1, wherein the mature heavy chain variable region has an amino acid sequence designated SEQ ID NO:9 and the mature light chain variable region has an amino acid sequence designated SEQ ID NO:5.

22. The antibody of claim 1, wherein the mature heavy chain variable region has an amino acid sequence designated SEQ ID NO:10 and the mature light chain variable region has an amino acid sequence designated SEQ ID NO:3.

23. The antibody of claim 1, wherein the mature heavy chain variable region has an amino acid sequence designated SEQ ID NO:10 and the mature light chain variable region has an amino acid sequence designated SEQ ID NO:4.

24. The antibody of claim 1, wherein the mature heavy chain variable region has an amino acid sequence designated SEQ ID NO:10, and is linked to a heavy chain constant region having an amino acid sequence designated SEQ ID NO:32 provided the C-terminal lysine may be omitted, and the mature light chain variable region has an amino acid sequence designated SEQ ID NO:5 and is linked to a light chain constant region having the amino acid sequence of SEQ ID NO:13 provided the N-terminal arginine of SEQ ID NO:13 may be omitted.

25. The antibody of claim 1, wherein the mature heavy chain variable region has an amino acid sequence designated SEQ ID NO:11 and the mature light chain variable region has an amino acid sequence designated SEQ ID NO:3.

26. The antibody of claim 1, wherein the mature heavy chain variable region has an amino acid sequence designated SEQ ID NO:11 and the mature light chain variable region has an amino acid sequence designated SEQ ID NO:4.

27. The antibody of claim 1, wherein the mature heavy chain variable region has an amino acid sequence designated SEQ ID NO:11 and the mature light chain variable region has an amino acid sequence designated SEQ ID NO:5.

28. The antibody of claim 1, wherein position L36 (Kabat numbering) is occupied by F and position H73 (Kabat numbering) is occupied by D, and position H93 (Kabat numbering) is occupied by S.

29. The antibody of claim 1, wherein position L36 (Kabat numbering) is occupied by F and position H93 (Kabat numbering) is occupied by S.

30. The antibody of claim 1, wherein position L36 (Kabat numbering) is occupied by F and position H73 (Kabat numbering) is occupied by D.

31. The antibody of claim 1, wherein position H73 (Kabat numbering) is occupied by D and position H93 (Kabat numbering) is occupied by S.

32. The antibody of claim 1, wherein position H93 (Kabat numbering) is occupied by S.

33. The antibody of claim 1, wherein position H73 (Kabat numbering) is occupied by D.

34. The antibody of claim 1, wherein position L36 (Kabat numbering) is occupied by F and position L83 (Kabat numbering) is occupied by L and position H73 (Kabat numbering) is occupied by D, and position H93 (Kabat numbering) is occupied by S.

35. The antibody of claim 1, wherein position L36 (Kabat numbering) is occupied by F and position L83 (Kabat numbering) is occupied by L and position H93 (Kabat numbering) is occupied by S.

36. The antibody of claim 1, wherein position L36 (Kabat numbering) is occupied by F and position L83 (Kabat numbering) is occupied by L and position H73 (Kabat numbering) is occupied by D.

37. The antibody of claim 1, wherein the mature heavy chain variable region is fused to a heavy chain constant region and the mature light chain constant region is fused to a light chain constant region.

38. The antibody of claim 37, wherein the heavy chain constant region has the amino acid sequence designated SEQ ID NO:14 provided the C-terminal lysine residue may be omitted.

39. The antibody of claim 37, wherein the light chain constant region has the amino acid sequence designated SEQ ID NO:13.

40. The antibody of claim 37, wherein the light chain has the constant region designated SEQ ID NO:28.

41. The antibody of claim 37, wherein the heavy chain constant region is a mutant form of natural human constant region which has reduced binding to an Fcy receptor relative to the natural human constant region.

42. The antibody of claim 37, wherein the heavy chain constant region is of human IgG1 isotype.

43. The antibody of claim 24, wherein the light chain constant region has the amino acid sequence of SEQ ID NO:13.

* * * * *

SEQUENCE LISTING

```
<160> NUMBER OF SEQ ID NOS: 32

<210> SEQ ID NO 1
<211> LENGTH: 113
<212> TYPE: PRT
<213> ORGANISM: Artificial Sequence
<220> FEATURE:
<223> OTHER INFORMATION: Synthesized

<400> SEQUENCE: 1

Asp Ile Val Met Ser Gln Ser Pro Ser Ser Leu Ala Val Ser Val Gly
1               5                   10                  15

Glu Lys Val Thr Met Ser Cys Lys Ser Ile Gln Thr Leu Leu Tyr Ser
            20                  25                  30

Ser Asn Gln Lys Asn Tyr Leu Ala Trp Phe Gln Gln Lys Pro Gly Gln
        35                  40                  45

Ser Pro Lys Leu Leu Ile Tyr Trp Ala Ser Ile Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

```
Tyr Tyr Ser Tyr Pro Leu Thr Phe Gly Ala Gly Thr Lys Leu Glu Leu
            100                 105                 110

Lys

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys
            100                 105

<210> SEQ ID NO 3
<211> LENGTH: 113
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 4
<211> LENGTH: 113
<212> TYPE: PRT
<213> ORGANISM: Artificial Sequence
<220> FEATURE:
<223> OTHER INFORMATION: Synthesized
```

```
<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
                100                 105                 110

Lys

<210> SEQ ID NO 5
<211> LENGTH: 113
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
                100                 105                 110

Lys

<210> SEQ ID NO 6
<211> LENGTH: 116
<212> TYPE: PRT
<213> ORGANISM: Artificial Sequence
<220> FEATURE:
<223> OTHER INFORMATION: Synthesized

<400> SEQUENCE: 6

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Ser Thr Tyr Tyr Pro Asp Asn Val
    50                  55                  60
```

Lys Gly Arg Phe Thr Ile Ser Arg Glu Asp Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ser Arg Gly Gly Ala Gly Ile Asp Tyr Trp Gly Gln Gly Thr Thr Leu
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Asp Met Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthesized

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthesized

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
            115

<210> SEQ ID NO 12
<211> LENGTH: 140
<212> TYPE: PRT
<213> ORGANISM: Artificial Sequence
<220> FEATURE:
<223> OTHER INFORMATION: Synthesized

<400> SEQUENCE: 12

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 330
<212> TYPE: PRT
<213> ORGANISM: Artificial Sequence
<220> FEATURE:
<223> OTHER INFORMATION: Synthesized

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 339
<212> TYPE: DNA
<213> ORGANISM: Artificial Sequence
<220> FEATURE:
<223> OTHER INFORMATION: Synthesized

<400> SEQUENCE: 15
gacatccaga tgacccagtc cccctcctcc ctgtccgcct ccgtgggcga ccgcgtgacc      60
atcacctgca gtccatcca gaccctgctg tactcctcca accagaagaa ctacctggcc     120
tggttccagc agaagcccgg caaggccccc aagctgctga tctactgggc ctccatccgc     180
aagtccggcg tgccctcccg cttctccggc tccggctccg gcaccgactt caccctgacc     240
atctcctccc tgcagcccga ggacttcgcc acctactact gccagcagta ctactcctac     300
cccctgacct cggcggcgg caccaagctg gagatcaag                             339

<210> SEQ ID NO 16
<211> LENGTH: 339
<212> TYPE: DNA
<213> ORGANISM: Artificial Sequence
<220> FEATURE:
<223> OTHER INFORMATION: Synthesized

<400> SEQUENCE: 16
gacatccaga tgacccagtc cccctcctcc ctgtccgcct ccgtgggcga ccgcgtgacc      60
atcacctgca gtccatcca gaccctgctg tactcctcca accagaagaa ctacctggcc     120
tggtaccagc agaagcccgg caaggccccc aagctgctga tctactgggc ctccatccgc     180
aagtccggcg tgccctcccg cttctccggc tccggctccg gcaccgactt caccctgacc     240
atctcctccc tgcagcccga ggacttcgcc acctactact gccagcagta ctactcctac     300
cccctgacct cggcggcgg caccaagctg gagatcaag                             339

<210> SEQ ID NO 17
<211> LENGTH: 339
<212> TYPE: DNA
<213> ORGANISM: Artificial Sequence
<220> FEATURE:
<223> OTHER INFORMATION: Synthesized

<400> SEQUENCE: 17
gacatccaga tgacccagtc cccctcctcc ctgtccgcct ccgtgggcga ccgcgtgacc      60
atcacctgca gtccatcca gaccctgctg tactcctcca accagaagaa ctacctggcc     120
tggttccagc agaagcccgg caaggccccc aagctgctga tctactgggc ctccatccgc     180
aagtccggcg tgccctcccg cttctccggc tccggctccg gcaccgactt caccctgacc     240
atctcctccc tgcagcccga ggacctggcc acctactact gccagcagta ctactcctac     300
cccctgacct cggcggcgg caccaagctg gagatcaag                             339

<210> SEQ ID NO 18
<211> LENGTH: 348
<212> TYPE: DNA
<213> ORGANISM: Artificial Sequence
<220> FEATURE:
<223> OTHER INFORMATION: Synthesized

<400> SEQUENCE: 18

```
gaggtgcagc tggtggagtc cggcggcggc ctggtgcagc ccggcggctc cctgcgcctg      60
tcctgcgccg cctccggctt caccttctcc aactacggca tgtcctgggt gcgccaggcc     120
cccggcaagg gcctggagtg ggtggcctcc atctcctccg gcggcggctc cacctactac     180
cccgacaacg tgaagggccg cttcaccatc tcccgcgacg acgccaagaa ctccctgtac     240
ctgcagatga actccctgcg cgccgaggac accgccgtgt actactgctc ccgcggcggc     300
gccggcatcg actactgggg ccagggcacc ctggtgaccg tgtcctcc                   348
```

<210> SEQ ID NO 19
<211> LENGTH: 348
<212> TYPE: DNA
<213> ORGANISM: Artificial Sequence
<220> FEATURE:
<223> OTHER INFORMATION: Synthesized

<400> SEQUENCE: 19

```
gaggtgcagc tggtggagtc cggcggcggc ctggtgcagc ccggcggctc cctgcgcctg      60
tcctgcgccg cctccggctt caccttctcc aactacggca tgtcctgggt gcgccaggcc     120
cccggcaagg gcctggagtg ggtggcctcc atctcctccg gcggcggctc cacctactac     180
cccgacaacg tgaagggccg cttcaccatc tcccgcgaca acgccaagaa ctccctgtac     240
ctgcagatga actccctgcg cgccgaggac accgccgtgt actactgctc ccgcggcggc     300
gccggcatcg actactgggg ccagggcacc ctggtgaccg tgtcctcc                   348
```

<210> SEQ ID NO 20
<211> LENGTH: 348
<212> TYPE: DNA
<213> ORGANISM: Artificial Sequence
<220> FEATURE:
<223> OTHER INFORMATION: Synthesized

<400> SEQUENCE: 20

```
gaggtgcagc tggtggagtc cggcggcggc ctggtgcagc ccggcggctc cctgcgcctg      60
tcctgcgccg cctccggctt caccttctcc aactacggca tgtcctgggt gcgccaggcc     120
cccggcaagg gcctggagtg ggtggcctcc atctcctccg gcggcggctc cacctactac     180
cccgacaacg tgaagggccg cttcaccatc tcccgcgacg acgccaagaa ctccctgtac     240
ctgcagatga actccctgcg cgccgaggac accgccgtgt actactgcgc ccgcggcggc     300
gccggcatcg actactgggg ccagggcacc ctggtgaccg tgtcctcc                   348
```

<210> SEQ ID NO 21
<211> LENGTH: 348
<212> TYPE: DNA
<213> ORGANISM: Artificial Sequence
<220> FEATURE:
<223> OTHER INFORMATION: Synthesized

<400> SEQUENCE: 21

```
gaggtgcagc tggtggagtc cggcggcggc ctggtgcagc ccggcggctc cctgcgcctg      60
tcctgcgccg cctccggctt caccttctcc aactacggca tgtcctgggt gcgccaggcc     120
```

```
cccggcaagg gcctggagtg ggtggcctcc atctcctccg gcggcggctc cacctactac    180
cccgacaacg tgaagggccg cttcaccatc tcccgcgaca acgccaagaa ctccctgtac    240
ctgcagatga actccctgcg cgccgaggac accgccgtgt actactgcgc ccgcggcggc    300
gccggcatcg actactgggg ccagggcacc ctggtgaccg tgtcctcc                 348
```

```
<210> SEQ ID NO 22
<211> LENGTH: 22
<212> TYPE: PRT
<213> ORGANISM: Artificial Sequence
<220> FEATURE:
<223> OTHER INFORMATION: Synthesized

<400> SEQUENCE: 22

Met Asp Met Arg Val Pro Ala Gln Leu Leu Gly Leu Leu Met Leu Trp
1               5                   10                  15

Val Ser Gly Ser Ser Gly
            20
```

```
<210> SEQ ID NO 23
<211> LENGTH: 66
<212> TYPE: DNA
<213> ORGANISM: Artificial Sequence
<220> FEATURE:
<223> OTHER INFORMATION: Synthesized

<400> SEQUENCE: 23
atggacatgc gcgtgcccgc ccagctgctg ggcctgctga tgctgtgggt gtccggctcc    60
tccggc                                                              66
```

```
<210> SEQ ID NO 24
<211> LENGTH: 19
<212> TYPE: PRT
<213> ORGANISM: Artificial Sequence
<220> FEATURE:
<223> OTHER INFORMATION: Synthesized

<400> SEQUENCE: 24

Met Glu Phe Gly Leu Ser Trp Leu Phe Leu Val Ala Ile Leu Lys Gly
1               5                   10                  15

Val Gln Cys
```

```
<210> SEQ ID NO 25
<211> LENGTH: 57
<212> TYPE: DNA
<213> ORGANISM: Artificial Sequence
<220> FEATURE:
<223> OTHER INFORMATION: Synthesized

<400> SEQUENCE: 25
atggagttcg gcctgtcctg gctgttcctg gtggccatcc tgaagggcgt gcagtgc       57
```

```
<210> SEQ ID NO 26
<211> LENGTH: 113
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 42
<223> OTHER INFORMATION: Xaa = Y or F
```

```
<220> FEATURE:
<221> NAME/KEY: VARIANT
<222> LOCATION: 89
<223> OTHER INFORMATION: Xaa = F or L

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Xaa Gln Gln Lys Pro Gly Lys
        35                  40                  45

Ala Pro Lys Leu Leu Ile Tyr Trp Ala Ser Ile Arg Lys Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Xaa Ala Thr Tyr Tyr Cys Gln Gln
                85                  90                  95

Tyr Tyr Ser Tyr Pro Leu Thr Phe Gly Gly Thr Lys Leu Glu Ile
            100                 105                 110

Lys

<210> SEQ ID NO 27
<211> LENGTH: 116
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 74
<223> OTHER INFORMATION: Xaa = N or D
<220> FEATURE:
<221> NAME/KEY: VARIANT
<222> LOCATION: 97
<223> OTHER INFORMATION: Xaa = A or S

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
50                  55                  60

Lys Gly Arg Phe Thr Ile Ser Arg Asp Xaa Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Xaa Arg Gly Gly Ala Gly Ile Asp Tyr Trp Gly Gln Thr Leu Val
            100                 105                 110

Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Synthesized
```

<400> SEQUENCE: 28

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 29
<211> LENGTH: 220
<212> TYPE: PRT
<213> ORGANISM: Artificial Sequence
<220> FEATURE:
<223> OTHER INFORMATION: Synthesized

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

```
<210> SEQ ID NO 30
<211> LENGTH: 219
<212> TYPE: PRT
<213> ORGANISM: Artificial Sequence
<220> FEATURE:
<223> OTHER INFORMATION: Synthesized

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 446
<212> TYPE: PRT
<213> ORGANISM: Artificial Sequence
<220> FEATURE:
<223> OTHER INFORMATION: Synthesized

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80
```

```
Leu Gln Met Asn Ser Leu Arg Ala Glu Asp Thr Ala Val Tyr Tyr Cys
             85                  90                  95

Ala Arg Gly Gly Ala Gly Ile Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Val Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 32
<211> LENGTH: 330
<212> TYPE: PRT
<213> ORGANISM: Artificial Sequence
<220> FEATURE:
<223> OTHER INFORMATION: Synthesized
```

```
<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```